United States Patent
Kanebako et al.

(10) Patent No.: US 11,065,435 B2
(45) Date of Patent: Jul. 20, 2021

(54) BLOOD PUMP AND BLOOD PUMP ADJUSTING METHOD

(71) Applicant: SUN MEDICAL TECHNOLOGY RESEARCH CORPORATION, Suwa (JP)

(72) Inventors: Hideki Kanebako, Nagano (JP); Takayuki Miyakoshi, Nagano (JP); Naofumi Miyajima, Nagano (JP)

(73) Assignee: SUN MEDICAL TECHNOLOGY RESEARCH CORPORATION, Nagano (JP)

( * ) Notice: Subject to any disclaimer, the term of this patent is extended or adjusted under 35 U.S.C. 154(b) by 0 days.

(21) Appl. No.: 16/489,202

(22) PCT Filed: Feb. 28, 2017

(86) PCT No.: PCT/JP2017/007876
§ 371 (c)(1),
(2) Date: Aug. 27, 2019

(87) PCT Pub. No.: WO2018/158838
PCT Pub. Date: Sep. 7, 2018

(65) Prior Publication Data
US 2019/0374691 A1     Dec. 12, 2019

(51) Int. Cl.
*A61M 60/419* (2021.01)
*A61M 60/50* (2021.01)
*A61M 60/148* (2021.01)

(52) U.S. Cl.
CPC ........ *A61M 60/419* (2021.01); *A61M 60/148* (2021.01); *A61M 60/50* (2021.01);
(Continued)

(58) Field of Classification Search
CPC ... A61M 1/1036; A61M 1/122; A61M 1/1086
(Continued)

(56) References Cited

U.S. PATENT DOCUMENTS 8,210,829 B2 * 7/2012 Horvath .............. F04D 13/0633
417/350
2013/0330219 A1 * 12/2013 LaRose .................. F04D 13/06
417/420

FOREIGN PATENT DOCUMENTS

JP     H9-51944 A     2/1997
JP     H9-317684 A    12/1997
(Continued)

OTHER PUBLICATIONS

International Search Report in PCT/JP2017/007876, dated Apr. 4, 2017, 2pp.

*Primary Examiner* — John R Downey
(74) *Attorney, Agent, or Firm* — Hauptman Ham, LLP

(57) ABSTRACT

A blood pump includes a blood supply mechanism; a motor having a stator, a rotor and a shaft; a base body; a casing; a fixed side slide member having a first slide surface and fixed to the base body; and a rotary side slide member. A second insertion hole allows the shaft to pass therethrough is in the rotary side slide member. The shaft is fitted into the second insertion hole between the fixed side slide member and the blood supply mechanism. The second slide surface is slidable on the first slide surface in contact with the first slide surface by rotating together with the blood supply mechanism and the shaft A center of the core is at a position more to a +z direction side than a center (CM) of a permanent magnet.

4 Claims, 13 Drawing Sheets

(52) U.S. Cl.
  CPC ............... *A61M 2205/332* (2013.01); *A61M 2205/3344* (2013.01); *A61M 2205/3365* (2013.01); *A61M 2205/3606* (2013.01)

(58) Field of Classification Search
  USPC ......................................................... 600/16
  See application file for complete search history.

(56) References Cited

FOREIGN PATENT DOCUMENTS

JP        2003-343490 A    12/2003
WO    2015/097916 A1    7/2015

\* cited by examiner

US 11,065,435 B2

BLOOD PUMP AND BLOOD PUMP ADJUSTING METHOD

RELATED APPLICATIONS

The present application is a National Phase of International Application Number PCT/JP2017/007876, filed Feb. 28, 2017.

TECHNICAL FIELD

The present invention relates to a blood pump and a blood pump adjusting method.

BACKGROUND ART

Conventionally, there has been known a blood pump where sealing is provided between a space of a pump chamber in which blood flows and a space in which mechanisms such as a shaft of a motor and bearings are housed using a mechanical seal (see patent literature 1 and patent literature 2, for example).

FIG. 15 a cross-sectional view of the blood pump 9 provided for explaining a conventional blood pump 9. Symbol 932 indicates an inflow port, and symbol 934 indicates an outflow port.

As shown in FIG. 15, the conventional blood pump 9 is the blood pump 9 where, using a blood supply mechanism 910 housed in a pump chamber Ra, blood is made to flow into the pump chamber Ra, is made to flow out from the pump chamber Ra, and is fed to the inside of a body of a user. The conventional blood pump 9 includes the blood supply mechanism 910, a motor 800, a base body 920, a bearing 982, a casing 930, a fixed side slide member 940, and a rotary side slide member 950. The fixed side slide member 940 and the rotary side slide member 950 form "mechanical seal".

The blood supply mechanism 910 is connected to one end of a shaft 830, and moves blood due to its rotation. The motor 800 includes a stator 810 (not having a core) and a rotor 820. The motor 800 also has the shaft 830 connected to the rotor 820. The motor 800 imparts rotational energy to the blood supply mechanism 910 by way of the shaft 830. A through hole (neither indicated by a symbol nor illustrated in the drawing) which allows the shaft 830 to pass therethrough is formed in the base body 920. The bearing 982 is connected to the base body 920. The casing 930 is fitted in the base body 920, and forms the pump chamber Ra together with the base body 920.

A first insertion hole 944 through which a shaft 830 passes is formed in the fixed side slide member 940, and the fixed side slide member 940 is fixed at the position corresponding to the through hole formed in the base body 920. The fixed side slide member 940 has a first slide surface 942.

A second insertion hole 954 through which the shaft 830 passes is formed in the rotary sides slide member 950, and the rotary side slide member 950 is interposed between the fixed side slide member 940 and the blood supply mechanism 910. The rotary side slide member 950 has a second slide surface 952. The shaft 830 is fitted in the second insertion hole 954 of the rotary side slide member 950. The rotary side slide member 950 rotates together with the blood supply mechanism 910 and the shaft 830, and the second slide surface 952 is slidable on the first slide surface 942 in contact with the first slide surface 942.

In the above-mentioned configuration, assume a rotary axis of the rotor 820 as a z axis, assume the direction along the z axis from a pump chamber Ra side toward a rotor 820 side as the +z direction, and assume the direction opposite to the +z direction as the −z direction.

A first permanent magnet 922a where a first magnetic pole, (for example, an N pole) is disposed on the +z direction side is connected to the bearing 982. On the other hand, a second permanent magnet 922b where a first magnetic pole (for example, an N pole) is disposed on the −z direction side is connected to the rotor 820. The first permanent magnet 922a and the second permanent magnet 922b are disposed such that the first magnetic pole of the first permanent magnet 922a and the first magnetic pole of the second permanent magnet 922b oppositely face each other (for example, the N poles oppositely facing each other), and the first permanent magnet 922a and the second permanent magnet 922b are disposed along the direction parallel to the z axis. The combination of the first permanent magnet 922a and the second permanent magnet 922b is referred to as a pair of permanent magnets 922.

In the conventional blood pump 9, the first permanent magnet 922a is connected to the bearing 982 and the base body 920, and is eventually integrally formed with the fixed side slide member 940. The second permanent magnet 922b is connected to the rotor 820 and the shaft 830, and is eventually configured such that the rotary side slide member 950 is moved in an interlocking manner with the second permanent magnet 922b along the z axis. In the above-mentioned configuration, the first permanent magnet 922a and the second permanent magnet 922b are disposed such that the same polarities (for example, N poles) oppositely face each other. With such a configuration, in the conventional blood pump 9, it is possible to generate a repulsive force between the first permanent magnet 922a and the second permanent magnet 922b in the direction parallel to the z axis. With the use of such a repulsive force, the shaft 830 can be pulled in the +z direction, and the second slide surface 952 of the rotary side slide member 950 can be pressed to the first slide surface 942 of the fixed side slide member 940 (a force which is generated by such pressing being referred to as "a pressing force applied to a seal slide surface of a mechanical seal" or being simply referred to as "pressing force"). In this manner, the above-mentioned configuration can exhibit a sealing effect as a mechanical seal formed of the rotary side slide member and the fixed side slide member (see paragraph [0030], paragraph [0038] and the like of patent literature 1, for example).

CITATION LIST

Patent Literature

PTL 1: JP 9-51944 A
PTL 2: JP 2003-343490 A

SUMMARY OF INVENTION

Technical Problem

However, for generating the above-mentioned pressing force, the conventional blood pump 9 additionally includes the first permanent magnet 922a and the second permanent magnet 922b (a pair of permanent magnets 922) besides permanent magnets (symbols and illustration of the permanent magnets not shown in the drawing) for rotating the motor 800. Due to such a configuration, in the blood pump 9, a volume for housing the first permanent magnet 922a and the second permanent magnet 922b is ensured.

On the other hand, since a thickness of a human chest is limited, in general, it is desirable that a volume of a blood pump be as small as possible. In the case where the volume of the blood pump is small and a weight of the blood pump is also small, for example, it is possible to embed the blood pump in the body of a human (user) having a small physique such as a child, for example, and hence, the number of persons to which the blood pump is applicable can be increased. Under such circumstances, the development of a blood pump having a smaller volume and a smaller weight has been eagerly anticipated.

In general, in a blood pump, assuming the case where a pressing force applied to a seal slide surface of a mechanical seal is excessively large, it is difficult for a liquid which contributes to a sealing effect to enter between a first slide surface and a second slide surface. In this case, lubrication during slide movement is lowered and hence, a load applied to a motor is also increased whereby energy efficiency is lowered. On the other hand, assuming the case where a pressing force applied to a mechanical seal is excessively small, the mechanical seal cannot exhibit a sealing effect.

Accordingly, it is necessary to control a pressing force applied to a seal slide surface of a mechanical seal to a value which is neither excessively large nor excessively small and falls within an appropriate range. That is, it is necessary to set a force by which a rotary side slide member is pressed to a fixed side slide member (pressing force) with high accuracy. On the other hand, in pursuing accuracy in setting a pressing force, in the case where the structure is adopted where a blood pump itself must repeat cumbersome disassembling and assembling, such a blood pump is not suitable from a viewpoint of productivity.

The present invention has been made in view of the above-mentioned circumstances, and it is an object of the present invention to provide a blood pump where a rotary side slide member can be pressed to a fixed side slide member without particularly providing an additional members (for example, the first permanent magnet and the second permanent magnet in the conventional blood pump 9 used in the case of the conventional blood pump) thus reducing a volume and a weight of the blood pump compared to conventional blood pumps.

It is also another object of the present invention to provide a blood pump which can adjust a force used for pressing a rotary side slide member to a fixed side slide member (pressing force) with high accuracy and efficiently.

It is also another object of the present invention to provide a blood pump adjusting method which can adjust a force used for pressing a rotary side slide member to a fixed side slide member (pressing force) with high accuracy and efficiently.

Solution to Problem

[1]

According to an aspect of the present invention, there is provided a blood pump which makes blood flow into a pump chamber, makes the blood flow out from the pump chamber, and makes the blood flow into the inside of a body of a user by a blood supply mechanism housed in the pump chamber, the blood pump including: the blood supply mechanism connected to one end of a shaft and capable of moving a liquid due to rotation thereof; a motor having a stator and a rotor, having the shaft connected to the rotor, and imparting rotational energy to the blood supply mechanism by way of the shaft; a base body having a pedestal portion which partitions the blood pump into a pump chamber side and a rotor side which is a side opposite to the pump chamber, wherein a through hole which allows the shaft to pass therethrough is formed in the base body at a position close to a center of the pedestal portion; a casing fitted into the base body thus forming the pump chamber together with the base body; a fixed side slide member having a first slide surface, wherein a first insertion hole which allows the shaft to pass therethrough is formed in the fixed side slide member, and the fixed side slide member is fixed to the base body at a position corresponding to the through hole; and a rotary side slide member having a second slide surface, wherein a second insertion hole which allows the shaft to pass therethrough is formed in the rotary side slide member, the shaft is fitted into the second insertion hole in a state where the shaft is interposed between the fixed side slide member and the blood supply mechanism, and the second slide surface is slidable on the first slide surface in a contact manner with the first slide surface by rotating together with the blood supply mechanism and the shaft, wherein the stator has a core around which a coil is wound, the rotor has a permanent magnet disposed so as to oppositely face a peripheral wall of the core, wherein an N pole and an S pole are alternately arranged along a circumferential direction that the rotor rotates, and assuming a rotary axis of the rotor as a z axis, a direction along the z axis extending from the pump chamber side to the rotor side as a +z direction, and a direction opposite to the +z direction as a −z direction, the stator is fixed to the base body, the rotor is movable relative to the stator along a direction parallel to the z axis, and a center of the core in the direction parallel to the z axis is located at a position shifted on a more +z direction side than a center of the permanent magnet in the direction parallel to the z axis.

In the blood pump according to the present invention, the center of the core in the direction parallel to the z axis is located at the position shifted on a more +z direction side than the center of the permeant magnet in the direction parallel to the z axis. With such a configuration, with respect to an attraction force generated between the core of the stator and the permanent magnet of the rotor, a component force parallel to the z axis is generated (this force being referred to as "given pressure" in this specification for a convenience purpose). With such a given pressure, the rotor and the shaft connected to the rotor are pulled in the +z direction. Then, the given pressure is transmitted to the rotary side slide member which is rotatable together with the blood supply mechanism and the shaft by way of the shaft. As a result, it is possible to press the second slide surface of the rotary side slide member to the first slide surface of the fixed side slide member with a force in the +z direction.

As can be also understood from the above description, in the blood pump according to the present invention, additional members (additional permanent magnets or the like) which are different from permanent magnets for rotating the motor are not particularly provided. Accordingly, a volume and a weight of the blood pump according to the present invention can be reduced compared to conventional blood pumps.

In this manner, according to the present invention, unlike the conventional blood pumps, it is possible to provide the blood pump where the rotary side slide member can be pressed to the fixed side slide member without particularly providing the additional members thus reducing a volume and a weight of the blood pump compared to the conventional blood pumps.

Further, by locating the position of the core of the stator at the desired position along the z axis (by setting the above-mentioned shift amount to a desired amount), a magnitude of a given pressure can be adjusted and, as a result, a force for pressing the second slide surface of the rotary side slide member to the first slide surface of the fixed side slide member (a pressing force on the seal slide surface of the mechanical seal) can be set to a value which falls within a desired range.

[2]

In the blood pump according to the present invention, it is preferable that the motor be an inner-rotor-type motor, a rotor housing space capable of housing the rotor be formed inside of the stator close to the z axis, and the rotor be housed in the rotor housing space in a state where the rotor is movable along the z axis.

In the case where the motor is an inner-rotor-type motor, a permanent magnet of the rotor is disposed at a position closer to a rotary axis (z axis) compared to the case where the motor is an outer-rotor-type motor. That is, a point of action at which a given pressure acts is disposed closer to the rotary axis. Accordingly, a given pressure transmitted to the rotary side slide member by way of the shaft can be transmitted in a stable state where irregularities are relatively small in the direction of the force, a magnitude of the force or the like. As a result, this configuration contributes to applying a pressing force to a seal slide surface of a mechanical seal with high accuracy.

[3]

In the blood pump according to the present invention, it is preferable that a shift amount of the center of the permanent magnet with respect to the center of the core fall within a range of from 0.2 mm to 1.0 mm inclusive.

By setting the shift amount of the permanent magnet to a value which falls within such a range, it is possible to provide the blood pump having a smaller volume and a smaller weight compared to the conventional blood pump while ensuring a necessary and sufficient given pressure.

[4]

In the blood pump according to the present invention, it is preferable that a liquid flow passage be provided where the liquid flow passage is surrounded by a surface facing in the +z direction among surfaces which form the rotary side slide member, an inner peripheral surface of the first insertion hole formed in the fixed side slide member, and any surface forming the shaft, and a given pressure in the +z direction given from the rotary side slide member to the fixed side slide member by way of the rotor and the shaft be set by taking into account a liquid pressure of a cooling liquid which passes through the liquid flow passage during an operation of the blood pump.

In the blood pump, there may be the case where, for example, the above-mentioned liquid flow passage is provided in the blood pump, and a cooling liquid (for example, cooling water) is made to circulate in the liquid flow passage so as to cool the whole motor including the shaft, the fixed side slide member, the rotary side slide member or the like.

A liquid pressure of the cooling liquid acts as a force in the direction that the rotary side slide member 50 is separated from the fixed side slide member 40 by pulling (a force in the −z direction). Accordingly, it is preferable that a given pressure applied by an adjustment ring 60 be set by taking into account the liquid pressure of the cooling liquid. With such a configuration, a pressing force for pressing the rotary side slide member 50 to the fixed side slide member 40 can be set to a value which falls within an appropriate range.

[5]

In the blood pump according to the present invention, it is preferable that the blood pump may further include a core position adjusting member having a screw portion on which threads are formed, the core position adjusting member being capable of moving the core in a direction parallel to the z axis while being engaged with any portion of the stator due to rotation of the screw portion.

By changing a rotation angle of the screw portion of the core position adjusting member, the position of the stator (in other words, the position of the core) can be adjusted by moving the position of the stator little by little in the direction parallel to the z axis. Accordingly, it is possible to perform the fine adjustment of a given pressure (eventually a pressing force) with high accuracy and efficiently.

In this manner, according to the present invention, it is possible to provide a blood pump where a force (a pressing force) by which the rotary side slide member is pressed to the fixed side slide member can be adjusted with high accuracy and efficiently.

[6]

In the blood pump having the above-mentioned configuration [5], it is preferable that the core position adjusting member be an adjustment ring having a circular cylindrical shape with the z axis set as a center of a circle, the core be disposed inside of the adjustment ring, and a lower peripheral edge of the adjustment ring protrude from a lower end portion of the core in the +z direction, first threads which form the screw portion be formed on an outer surface of the adjustment ring, and an engaging protruding portion be formed on an upper peripheral edge of the adjustment ring, a side wall portion protruding in a circular cylindrical shape in the +z direction from an outer edge of the pedestal portion be formed on the base body, and second threads be formed on an inner wall of the side wall portion, the first threads and the second threads threadedly engage with each other, and the engaging protruding portion of the adjustment ring be brought into contact with an upper end portion of the core, and the core which is brought into contact with the engaging protruding portion be configured to be movable along the z axis due to the movement of the engaging protruding portion along the z axis caused by rotation of the adjustment ring.

In this manner, the first threads formed on the outer surface of the adjustment ring and the second threads formed on the inner wall of the side wall portion of the base body engage with each other. Accordingly, by rotating the adjustment ring by applying a force to the adjustment ring in the circumferential direction of the adjustment ring, the engaging protruding portion of the adjustment ring can be moved along the z axis. Due to the movement of the engaging protruding portion along the z axis, the core which is brought into contact with the engaging protruding portion can be also moved along the z axis. In this manner, the position of the core can be moved along the z axis by rotating the adjustment ring.

Particularly, a rotating portion of the adjustment ring has a large diameter compared to a core position adjustment member formed of a feeding screw or the like. Accordingly, even when a periphery of the adjustment ring is largely moved in the circumferential direction, the displacement of a rotation angle brought about by such movement of the adjustment ring is relatively small. Further, the adjustment ring has a circular cylindrical shape and hence, first threads can be formed on an outer surface of the adjustment ring at a relatively narrow pitch with high accuracy. Further, with the use of the adjustment ring, it is possible to provide a mechanism where even when the adjustment ring is moved in the circumferential direction with a large operation amount, such a large operation amount is converted into a small moving amount of the adjustment ring in the direction parallel to the z axis.

Accordingly, with the provision of the adjustment ring, the position of the core can be adjusted with high accuracy. As a result, it is possible to adjust a given pressure with high accuracy and efficiently.

The lower peripheral edge of the circular sleeve of the adjustment ring protrudes from the lower end portion of the core in the +z direction. Accordingly, the lower peripheral edge of the circular sleeve of the adjustment ring can be gripped without being obstructed by the core and the adjustment ring can be easily rotated.

In the blood pump having the above-mentioned configuration [6], the second threads are formed on the base body. However, the present invention is not limited to such a configuration. For example, the configuration may be adopted where the second threads are formed on a different member, and the positional relationship between the adjustment ring and the base body can be indirectly adjusted by connecting the different member and the base body to each other. The blood pump having such a configuration is also an equivalent of the blood pump having the above-mentioned configuration [6].

[7]

In the blood pump having the above-mentioned configuration [6], it is preferable that the blood pump further include a stator fixing ring fitted on an inner side of the adjustment ring such that the stator fixing ring is brought into contact with a lower end portion of the core.

With such a configuration, the core is sandwiched between the stator fixing ring and the engaging protruding portion of the adjustment ring. Accordingly, the position of the core is further firmly fixed and hence, there is no possibility that the core is displaced toward the z axis direction.

[8]

According to another aspect of the present invention, there is provided a blood pump adjusting method for adjusting the blood pump having the above-mentioned configuration [6] or [7]. The blood pump adjusting method includes: a blood pump preparation step of preparing an adjustment state blood pump where at least a portion of the shaft on the +z direction side is exposed; an adjustment jig mounting step having: a step of holding the adjustment state blood pump by a blood pump holder; and a step of connecting a controller for controlling the adjustment state blood pump to the adjustment state blood pump; and a runtime adjustment step having: an F gauge contacting and pressing step of bringing a probe of a force gauge into contact with a center of rotation of the shaft from a +z direction side of the shaft and of pressing the probe; a motor rotation step of rotating the motor of the adjustment state blood pump at a predetermined condition; a pressing force measurement step of measuring a pressing force by reading a value of the force gage; a first adjustment step of moving the core in the +z direction by rotating the adjustment ring in a first rotational direction in a case where it is determined that a measured pressing force is lower than a lower limit value of a predetermining control range; and a second adjustment step of moving the core in a −z direction by rotating the adjustment ring in a second rotational direction opposite to the first rotational direction in a case where it is determined that the measured pressing force is higher than an upper limit value of the predetermining control range.

According to the blood pump adjusting method of the present invention, by performing the first adjustment step and the second adjustment step while measuring an actual pressing force in the pressing force measurement step using a currently using blood pump, it is possible to adjust an actual pressing force to a value which falls within an appropriate range.

Accordingly, a force (a pressing force) by which the rotary side slide member presses the fixed side slide member can be adjusted with high accuracy and efficiently.

BRIEF DESCRIPTION OF DRAWINGS

FIG. 11 is the cross-sectional view of a motor 100 taken along a plane perpendicular to a z axis.

FIG. 13 is a cross-sectional view of a main part of a blood pump 1a according to a modification 1 for describing the blood pump 1a.

FIG. 14 is a cross-sectional view of a main part of a blood pump 2a according to a modification 2 for describing the blood pump 2a.

DESCRIPTION OF EMBODIMENTS

Hereinafter, a blood pump and a blood pump adjusting method according to the present invention are described with reference to embodiments shown in drawings. The respective drawings are schematic views, and do not always strictly reflect actual sizes.

Embodiment 1

1. Basic Configuration of Blood Pump 1 According to Embodiment 1

Figure 1:
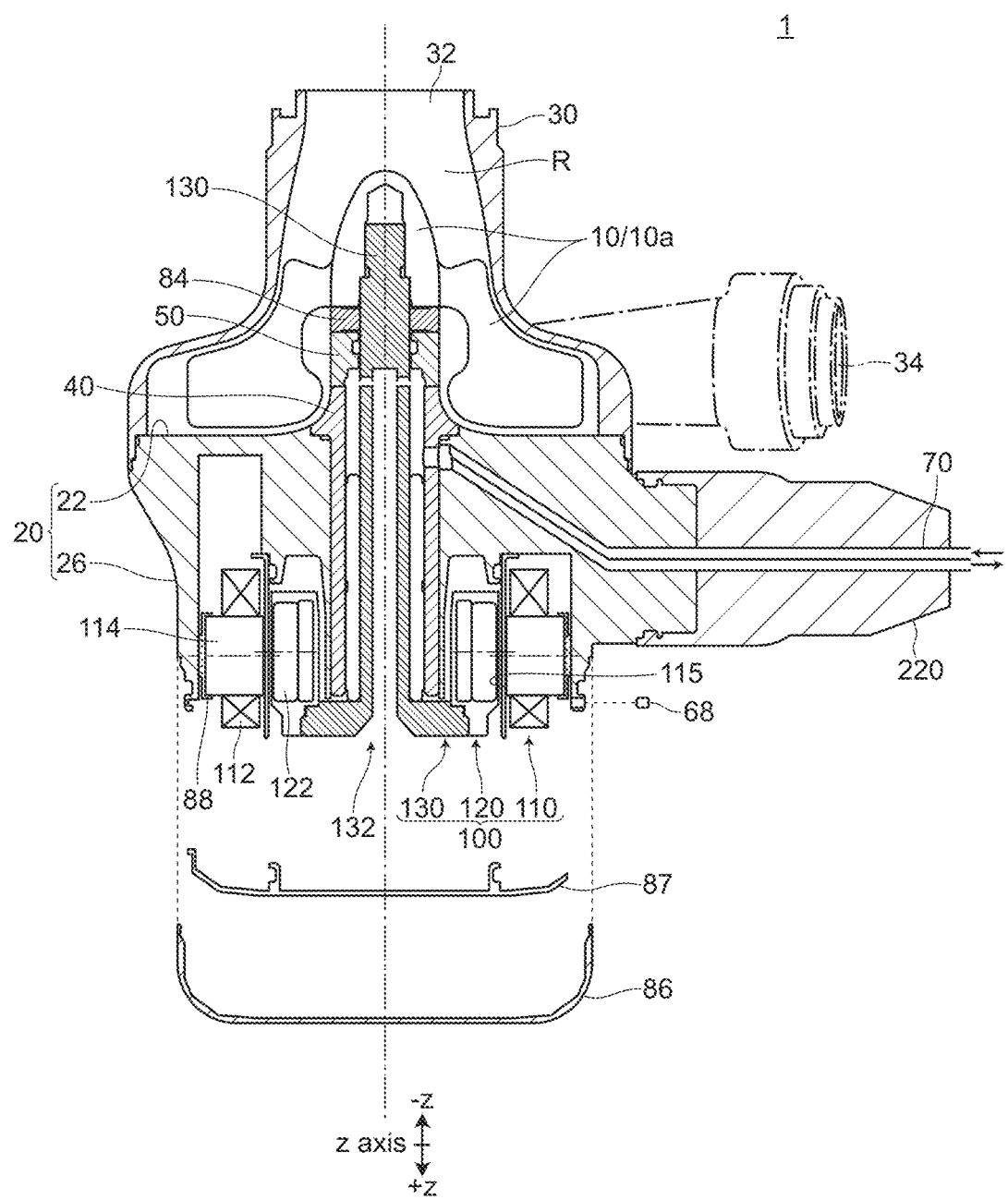
FIG. 1 is a cross-sectional view of a blood pump 1 according to an embodiment 1 for describing the blood pump 1.
Figure 2:
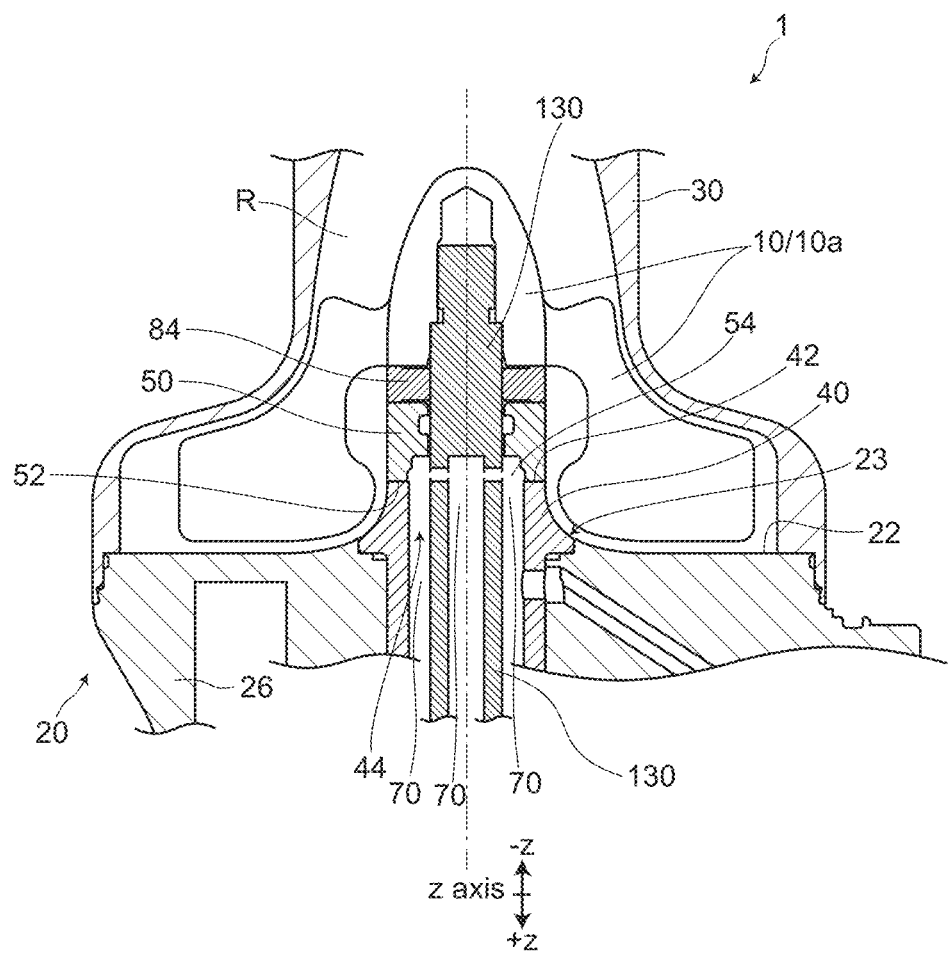
FIG. 2 is a cross-sectional view of a main part of the blood pump 1 according to the embodiment 1 for describing the blood pump 1.
Figure 3A:
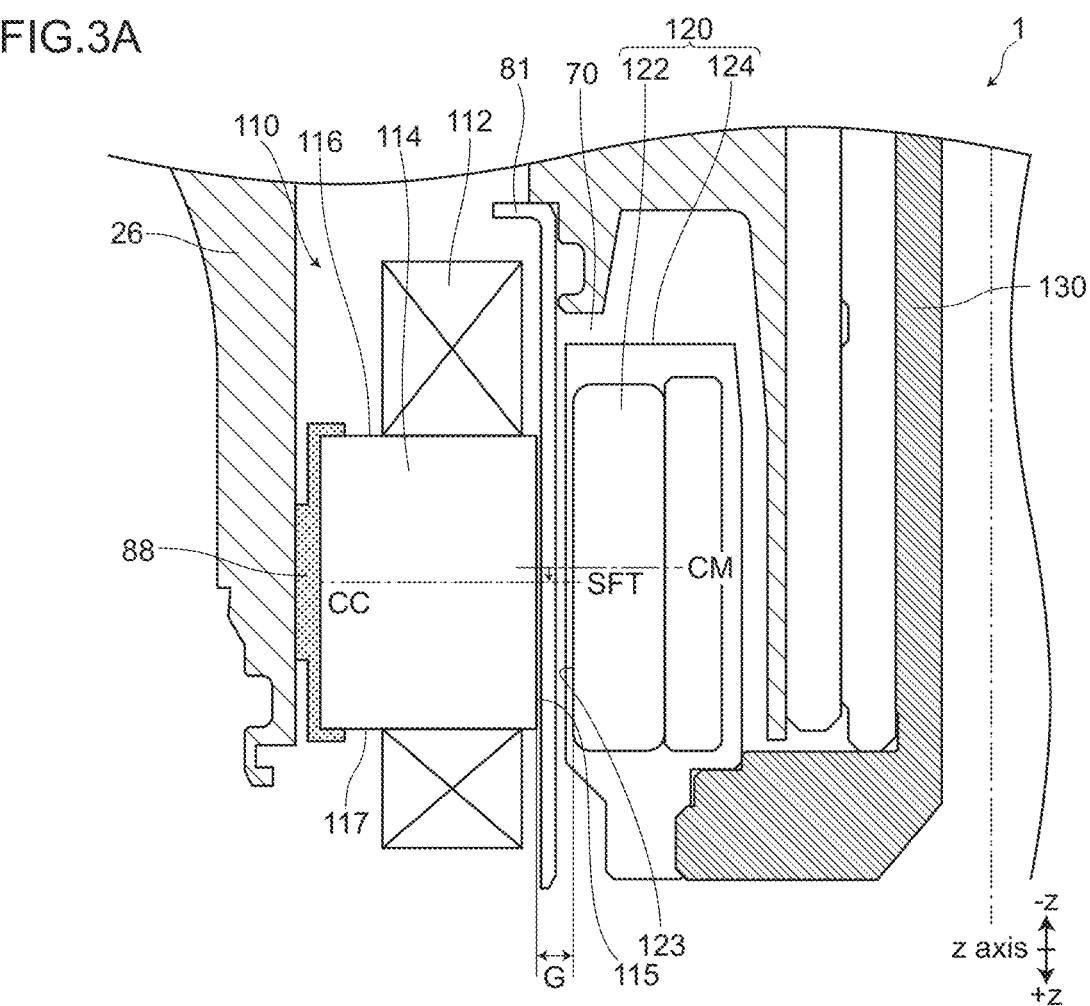
FIG. 3A and FIG. 3B are cross-sectional views of a main part of the blood pump 1 according to the embodiment 1 for describing the blood pump 1.
Figure 3B:
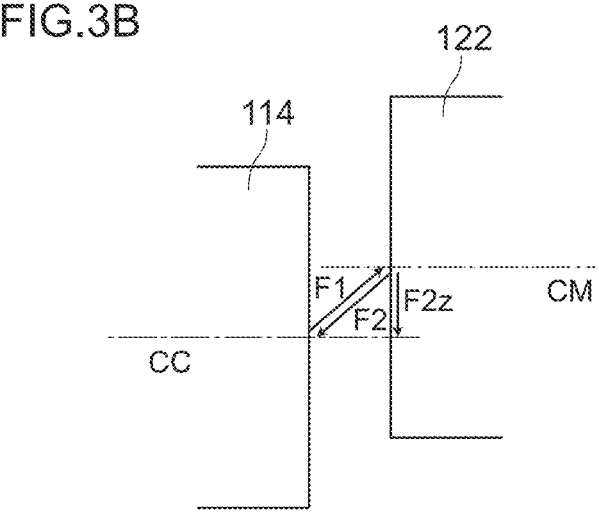

FIG. 1 is a cross-sectional view of the blood pump 1 according to the embodiment 1 for describing the blood pump 1. FIG. 1 shows the blood pump 1 in a state where a back lid 86, a back lid seal 87, and hexagon socket set screws 68 are removed from a body side of the blood pump 1. FIG. 2 is a cross-sectional view of a main part of the blood pump 1 according to the embodiment 1 for describing the blood pump 1. A rotor 120, a stator 110 and the like which ought to appear outside a wavy line are not shown in FIG. 2. FIG. 3A and FIG. 3B are cross-sectional views of a main part of the blood pump 1 according to the embodiment 1 for describing the blood pump 1. In FIG. 3A, a blood supply mechanism 10, a casing 30, the back lid 86, the back lid seal 87 and the like are not shown in FIG. 3A. FIG. 3B is a schematic view for describing an attractive force generated between cores 114 and permanent magnets 122 in detail.

The blood pump 1 according to the embodiment 1 is the blood pump 1 where, using the blood supply mechanism 10 housed in a pump chamber R, blood is made to flow into the pump chamber R through an inflow port 32, is made to flow out from the pump chamber R through an outflow port 34, and is fed to the inside of a body of a user. The blood pump 1 includes the blood supply mechanism 10, a motor 100, a base body 20, a casing 30, a fixed side slide member 40, and a rotary side slide member 50 (see FIG. 1). The fixed side slide member 40 and the rotary side slide member 50 form "mechanical seal".

The base body 20 is a portion which forms a base in assembling the blood pump 1. The base body 20 has a pedestal portion 22 which partitions the blood pump 1 into a pump chamber R side and a rotor 120 (described later) side which is a side opposite to the pump chamber R. Using the pedestal portion 22 as a boundary, blood flows on the pump chamber R side. When the pedestal portion 22 is viewed in a +z direction (described later), a through hole 23 which allows a shaft 130 (described later) to pass therethrough is formed in the pedestal portion 22 at a position close to the center of the pedestal portion 22 (see FIG. 1 and FIG. 2).

The casing 30 is fitted into the base body 20 thus forming the pump chamber R together with the base body 20.

The blood supply mechanism 10 has a function of moving a liquid due to its rotation. As the blood supply mechanism 10, any mechanism having such a function can be adopted. For example, a mechanism which uses an impeller (such as a centrifugal impeller, an axial impeller or the like), a mechanism which uses flagella or the like can be adopted.

The blood supply mechanism 10 is housed in the pump chamber R surrounded by the pedestal portion 22 of the base body 20 and the casing 30.

The motor 100 has the stator 110, the rotor 120, and the shaft 130 connected to the rotor 120. The blood supply mechanism 10 is connected to one end of the shaft 130. The motor 100 imparts rotational energy to the blood supply mechanism 10 by way of the shaft 130.

The stator 110 has at least the cores 114 and coils 112. The coil 112 is wound around the core 114. A member made of any material can be adopted as the core 114 provided that the member has magnetic property. However, it is preferable to use a member made of iron or the like which is a ferromagnet.

The rotor 120 is a member which forms a rotary portion, and has at least permanent magnets 122.

The permanent magnets 122 are arranged so that the permanent magnet 122 opposedly faces a peripheral wall (inner peripheral wall 115) of the core 114.

In this embodiment, "peripheral wall of the core" means a wall of the core 114 along a circumferential direction about a rotary axis. In an inner-rotor-type motor, an inner peripheral wall of a core corresponds to "the peripheral wall of the core" (see the inner peripheral wall 115 shown in FIG. 1, FIG. 3A and FIG. 3B). In an outer-rotor-type motor, an outer peripheral wall of a core corresponds to "the peripheral wall of the core".

In the permanent magnets 122, an N pole and an S pole are alternately arranged along the circumferential direction along which the rotor 120 rotates.

The shaft 130 is configured to integrally rotate with the rotor 120, and to move in the direction parallel to the z axis integrally with the rotor 120. For example, the shaft 130 may be connected with the rotor 120 in the form where the shaft 130 is fitted into the rotor 120. Alternatively, a trunk portion (not shown in the drawing) of the rotor 120 may be integrally formed with the shaft 130 by molding.

In this embodiment, a rotary axis of the rotor 120 is defined as "z axis", the direction along the z axis extending from a pump chamber R side to a rotor 120 side is defined as "+z direction", and the direction opposite to the +z direction is defined as "−z direction". For reference purposes, in a usual case, a rotary axis of the shaft 130 is also aligned with the z axis.

The fixed side slide member 40 has a first slide surface 42, and a first insertion hole 44 into which the shaft 130 is insertable is formed in the fixed side slide member 40. The fixed side slide member 40 is fixed to the base body 20 at a position corresponding to the through hole 23 formed in the base body 20. For example, in FIG. 1 and FIG. 2, the fixed side slide member 40 is inserted into the first insertion hole 44 at the position which corresponds to the through hole 23 formed in the base body 20. The fixed side slide member 40 is fixed in the form where the first slide surface 42 appears from the pedestal portion 22 on the −z direction side.

The rotary side slide member 50 has a second slide surface 52. A second insertion hole 54 which allows the insertion of the shaft 130 is formed in the rotary side slide member 50.

The rotary side slide member 50 is fitted on the shaft 130 in a state where the rotary side slide member 50 is interposed between the fixed side slide member 40 and the blood supply mechanism 10 (the shaft 130 being fitted in the rotary side slide member 50 in a state where the shaft 130 is inserted into the second insertion hole 54). In other words, the blood supply mechanism 10, the rotary side slide member 50, and the fixed side slide member 40 are disposed on the shaft 130 in this order from an upper portion (−z direction side) to a lower portion (+z direction side) of the shaft 130. The second slide surface 52 of the rotary side slide member 50 is brought into contact with the first slide surface 42 of the fixed side slide member 40.

The rotary side slide member 50 is connected to the blood supply mechanism 10 which is connected to one end of the shaft 130 such that the rotary side slide member 50 is integrally rotatable with the blood supply mechanism 10. A so-called cushion ring 84 is interposed between the rotary side slide member 50 and the blood supply mechanism 10.

With such a configuration, the rotary side slide member 50 rotates together with the blood supply mechanism 10 and the shaft 130, and the second slide surface 52 is slidable in contact with the first slide surface 42.

On the other hand, the stator 110 is fixed to the base body 20. In this embodiment, it is sufficient that the cores 114 which form the stator 110 are fixed to the base body 20 in any suitable form. In such a configuration, "fixed" may be a state where the movement of the stator 110 relative to the base body 20 in the direction parallel to at least the z axis is prevented. The stator 110 may be directly connected and fixed to the base body 20. Further, for example, the stator 110 may be indirectly connected and fixed to the base body 20 by means of another member such as the fixed member 88 shown in FIG. 1, FIG. 3A and FIG. 3B.

On the other hand, the rotor 120 is movable relative to the stator 110 along the direction parallel to the z axis. In this embodiment, "movable" is construed so that the rotor 120 is movable to an extent that the rotor 120 does not interfere with another member so that the rotation of the rotor 120 is not obstructed.

In the blood pump 1 according to the embodiment 1, as shown in FIG. 3A, the center CC of the core 114 in the direction parallel to the z axis is located at the position shifted toward the +z direction side from the center CM of the permanent magnet 122 in the direction parallel to the z axis. In other words, the center CC of the core 114 is located at the position slightly displaced toward the +z direction side from the center CM of the permanent magnet 122.

To consider the case where when the permanent magnet 122 is placed at a neutral state (the permanent magnet 122 being placed in a state where the permanent magnet 122 is not affected by other magnetic elements), lines of magnetic force generated from the permanent magnet 122 are distributed in line symmetry, in this embodiment, "the center CM of the permanent magnet 122" is the position which becomes an axis of symmetry with respect to such line symmetry. In general, the permanent magnet 122 has a fixed height along the direction parallel to the z axis. In the case where it is regarded that a magnetic element is uniformly formed (for example, it is regarded that the magnetic element is uniformly magnetized) along the direction parallel to the z axis on the outer peripheral surface 123 of the permanent magnet, the position of a middle point of the height of the permanent magnet 122 corresponds to "the center CM of the permanent magnet 122".

"the center CC of the core 114" is substantially defined in the same manner as the above. In the case where it is regarded that a magnetic element is uniformly formed along the direction parallel to the z axis on the inner peripheral wall 115 of the core 114, the position of a middle point of the height of the core 114 corresponds to "the center CC of the core 114".

The rotor 120, the shaft 130, the blood supply mechanism 10, the cushion ring 84, the rotary side slide member 50 and the like form "rotary portion". The stator 110, the base body 20, the fixed side slide member 40 and the like form "fixed portion".

2. Manner of Operation and Advantageous Effects of Blood Pump 1 According to Embodiment 1

Next, the manner of operation and the advantageous effects of the blood pump 1 according to the embodiment 1 are described with reference to FIG. 3A and FIG. 3B.

(1) Assume that the permanent magnet 122 attracts the core 114 with a force "F1" shown in FIG. 3B. Due to a reaction, the core 114 attracts the permanent magnet 122 with a force "F2" having a relationship with the force F1 where the force F2 has the same magnitude of force with the force F1 and has the direction of force opposite to the direction of force of the force F1. That is, the permanent magnet 122 and the core 114 impart an attractive force to each other.

In the present invention, the blood pump 1 according to the embodiment 1 includes the motor in which the rotor 120 which forms a rotary body is incorporated. Accordingly, as a matter of course, the core 114 and the permanent magnet 122 are spaced apart from each other with an air gap G formed therebetween (see FIG. 3A). Further, in the blood pump 1 according to the embodiment 1, the center CC of the core 114 in the direction parallel to the z axis is located at the position shifted toward the +z direction side from the center CM of the permanent magnet 122 in the direction parallel to the z axis (a shift amount indicated by symbol SFT in FIG. 3A).

In this manner, the blood pump 1 according to the embodiment 1 adopts the configuration where the center CC of the core 114 is shifted toward the +z direction side from the center CM of the permanent magnet 122. Accordingly, the force F2 with which the core 114 attracts the permanent magnet 122 has a component F2z which is parallel to the z axis is generated (the component F2z parallel to the z axis in the attractive force F2 is referred to as "given pressure" for the sake of convenience in this specification).

With such a given pressure F2z, the permanent magnet 122 is pulled toward the +z direction.

Since the rotor 120 is movable relative to the stator 110 along the direction parallel to the z axis, due to the above-mentioned give pressure F2z, the rotor 120 including the permanent magnet 122 and the shaft 130 connected to the rotor 120 are pulled in the +z direction.

The given pressure F2z is also transmitted to the rotary side slide member 50 which is rotatable together with the blood supply mechanism 10 and the shaft 130 toward the +z direction by way of the shaft 130.

As a result, it is possible to press the second slide surface 52 of the rotary side slide member 50 to the first slide surface 42 of the fixed side slide member 40 with a force in the +z direction (a force which corresponds to the given pressure F2z ) (see also FIG. 2).

In this manner, according to the embodiment 1, it is possible to provide the blood pump 1 where the rotary side slide member 50 can be pressed to the fixed side slide member 40 without particularly providing an additional members used in the case of the conventional blood pump 9 thus reducing a volume and a weight of the blood pump 1 compared to the conventional blood pump 9.

To describe for reference purposes, when the motor 100 rotates, an electric current in a predetermined direction flows in the coils 112, and an N pole and an S pole appear alternately in the respective coils 112 and the cores 114 corresponding to the respective coils 112. On the other hand, due to the rotation of the rotor 120 side, an N pole and an S pole of the permanent magnets 122 also alternately appear on front surfaces of the respective cores. In this case, at a glance, it appears that the above-mentioned given pressure F2z is not generated in the motor 100 as a whole at a moment when a repulsive force is generated between the permanent magnet 122 and the core 114.

However, although the above-mentioned "repulsive force" may be generated in one core, an electric current having a phase different from a phase of an electric current which flows in the coil corresponding to one core flows in another core, and in still another core, polarity of the permanent magnet 122 which oppositely faces the core becomes polarity different from polarity of the permanent magnet which oppositely faces one core. That is, "attractive force" is generated in another core and still another core and hence, eventually, the occurrence of the case where "repulsive force" becomes superior to "attractive force" in the motor 100 as a whole is avoided.

Further, in general, a state where the position of the center CC of the core is aligned with the position of the center CM of the permanent magnet is the most stable state for the motor. Accordingly, if the position of the center CC of the core is displaced from the center CM of the permanent magnet, a force which brings the motor into a state close to the above-mentioned stable state is generated. Accordingly, also from a macroscopic view, the permanent magnet 122 and the core 114 impart attractive forces (F1 and F2) to each other and hence, eventually, it is possible to obtain the component (F2z) in the direction parallel to the z axis.

(2) A distribution state of lines of magnetic force generated from the permanent magnet 122 differs depending on a positional relationship/a distance between a point where the distribution of the lines of magnetic force is focused and the permanent magnet 122. By making use of such a condition, it is possible to change a magnitude of the attractive force generated between the core 114 and the permanent magnet 122 by suitably changing the position of the core 114 with respect to the permanent magnet 122.

That is, it is possible to suitably set the magnitude of the attractive force by locating the position of the center CC of the core 114 at the desired appropriate position along the z axis with respect to the center CM of the permanent magnet 122. By setting of the magnitude of the attractive force in this manner, a magnitude of a component parallel to the z axis of the attractive force (given pressure F2z) can be also set. By suitably setting the given pressure F2z to an appropriate magnitude, eventually, it is possible to set a force which presses the second slide surface 52 of the rotary side slide member 50 to the first slide surface 42 of the fixed side slide member 40 (a pressing force on the seal slide surface of the mechanical seal) to a value which falls within a desired range.

3. Ventricular Assist System 5 which uses Blood Pump 1

Figure 4:
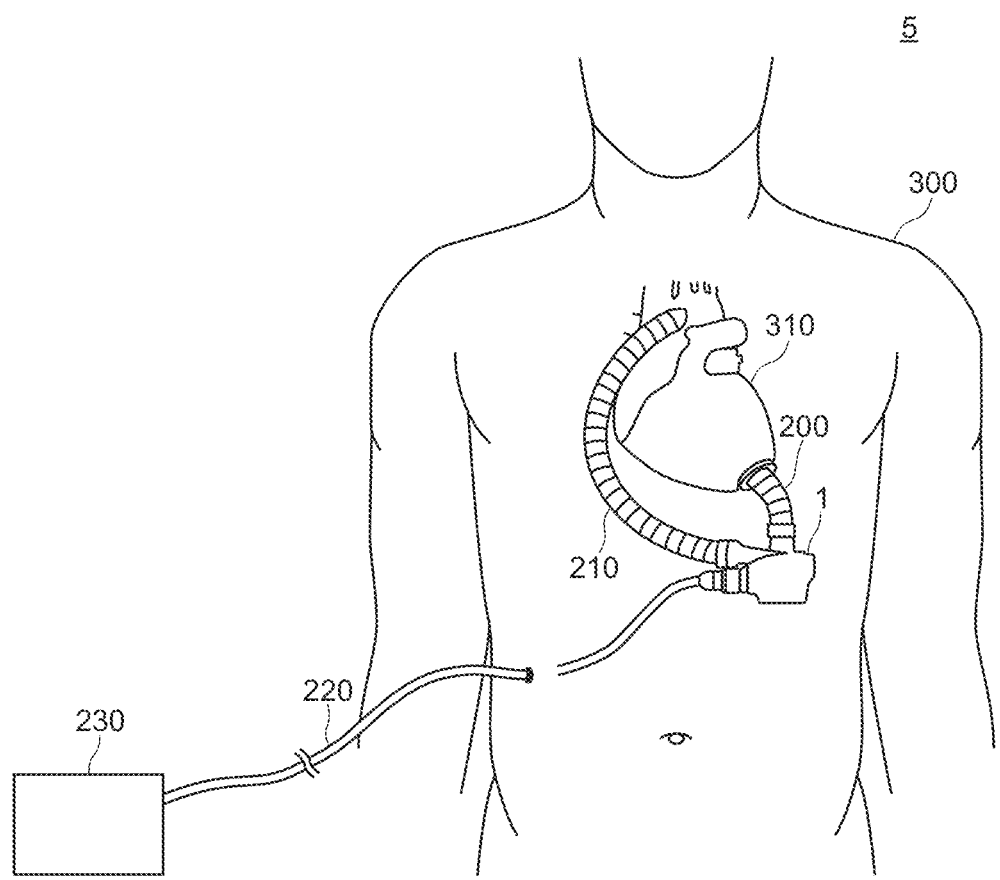
FIG. 4 is a view schematically showing a ventricular assist system 5 for describing the ventricular assist system 5 in the case where the blood pump 1 according to the embodiment 1 is embedded in a human body.

FIG. 4 is a view schematically showing a ventricular assist system 5 for describing the ventricular assist system 5 in the case where the blood pump 1 according to the embodiment 1 is embedded in a human body.

For example, as shown in FIG. 4, the ventricular assist system 5 includes: the blood pump 1 which is embedded in a body of a user 300; an artificial blood vessel 200 which connects the blood pump 1 and a left ventricle (not shown in the drawings) of an actual heart 310 of the user 300; an artificial blood vessel 210 provided for returning blood from the blood pump 1 to a living body of the user; a controller 230 disposed outside the body of the user; a tube 220 which connects the controller 230 and the blood pump 1 to each other and the like.

The controller 230 controls the operation of the blood pump 1. At the same time, the controller 230 supplies a liquid for cooling (cooling water) to the blood pump 1 on one hand, and recovers liquid for cooling water (cooling water) from the blood pump 1 on the other hand. In the tube 220, a cable (not shown in the drawings) which connects the controller 230 and the blood pump 1 to each other and a pipe (not shown in the drawings) through which a cooling liquid passes are disposed.

As has been described heretofore, the blood pump 1 according to the embodiment 1 can have a smaller volume and a smaller weight compared to a conventional blood pump. With the use of such a blood pump 1, for example, it is possible to embed the blood pump 1 in the body of a human (patient) having a small physique such as a child. Accordingly, it is expected that the number of people to which the blood pump is applicable can be increased.

In this specification, it is expressed that the blood pump is "embedded" in the body. Alternatively, it may be expressed that the blood pump is "implanted" in the body.

The blood pump 1 according the embodiment 1 may be disposed outside the body of the user.

Embodiment 2

Next, a blood pump 2 according to the embodiment 2 is described with reference to FIG. 5 and FIG. 6.

Figure 5:
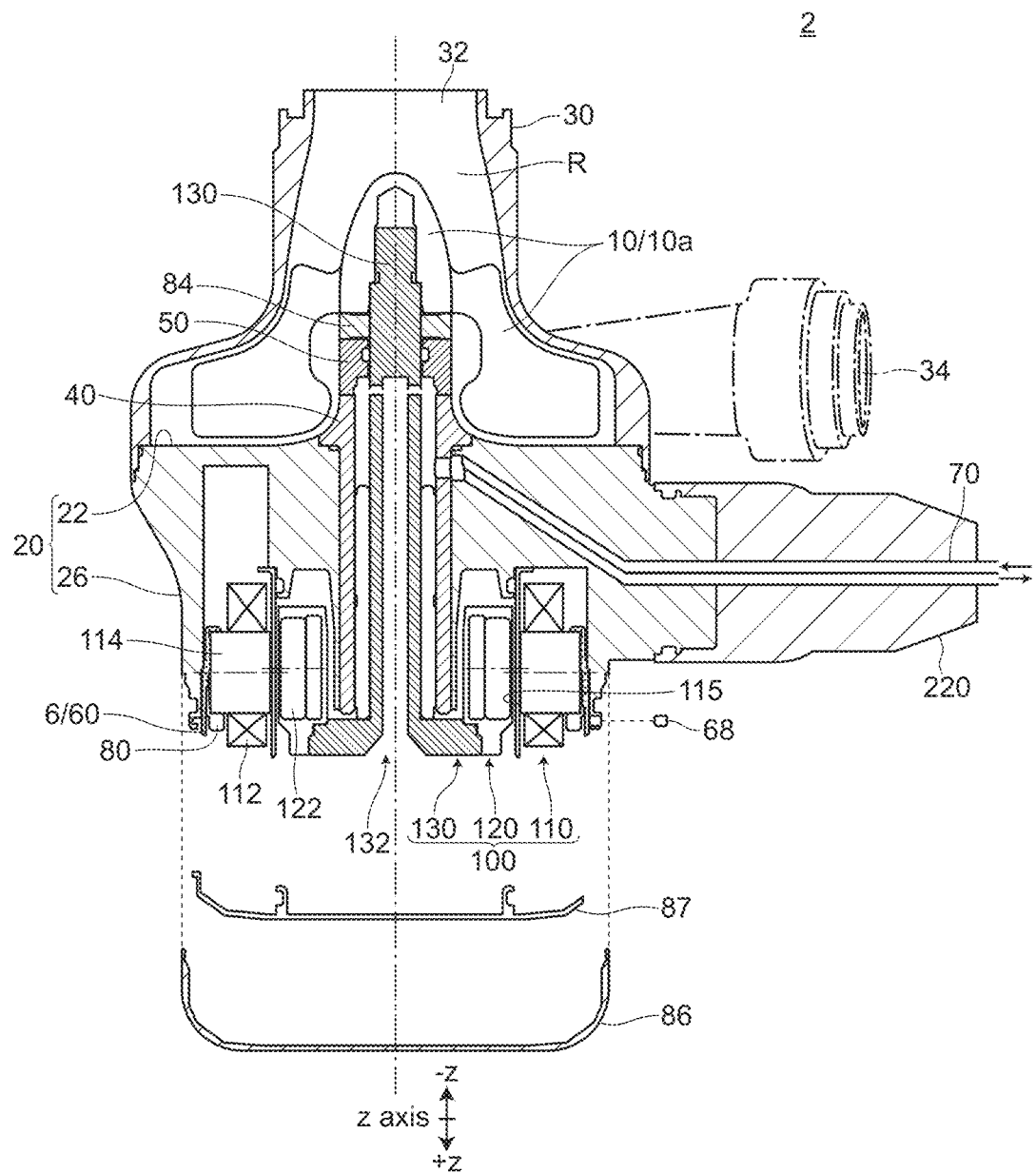
FIG. 5 is a cross-sectional view of a blood pump 2 according to an embodiment 2 for describing the blood pump 2.

FIG. 5 is a cross-sectional view of the blood pump 2 according to the embodiment 2 for describing the blood pump 2. The blood pump 2 is shown in a state where a back lid 86, a back lid seal 87 and a hexagon socket set screw 68 are removed from a blood pump 2 body side. FIG. 6 is a cross-sectional view of a main part of the blood pump 2 according to the second embodiment for describing the blood pump 2.

Figure 6:
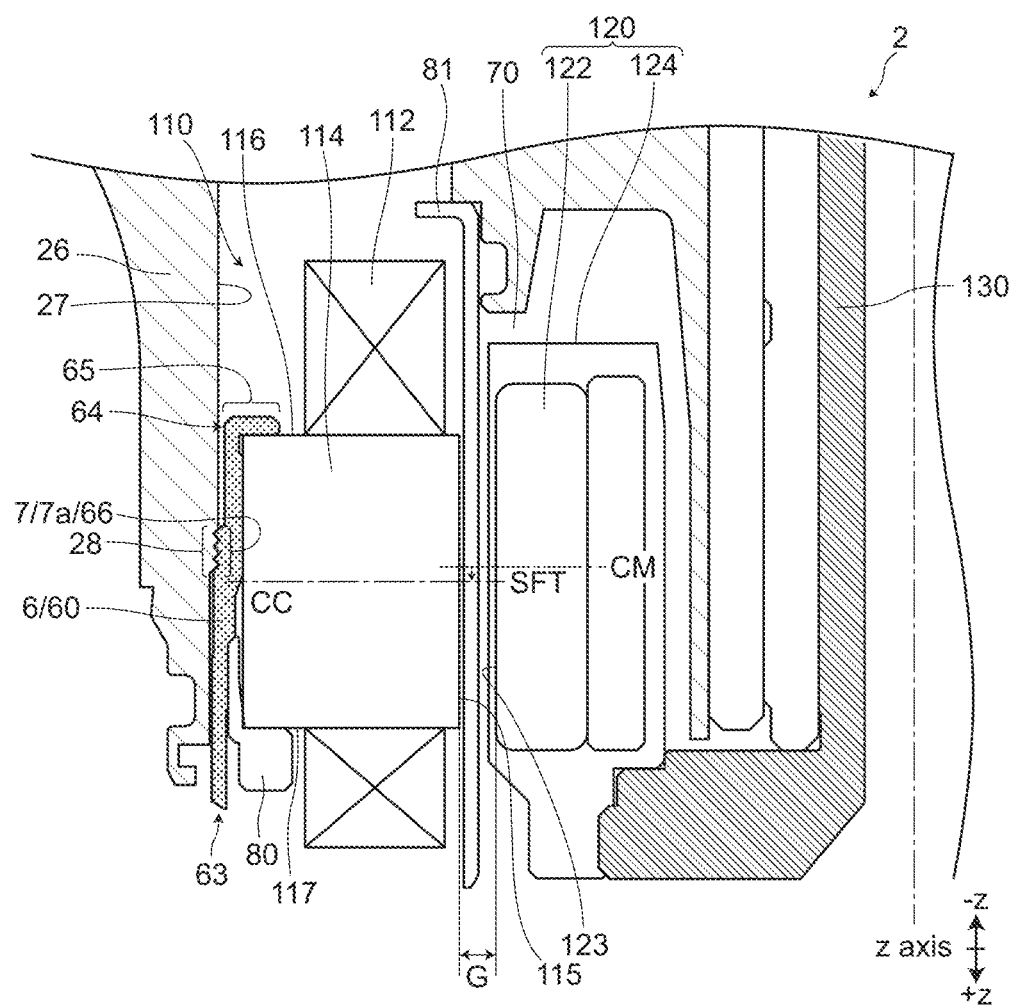
FIG. 6 is a cross-sectional view of a main part of the blood pump 2 according to the embodiment 2 for describing the blood pump 2.

In FIG. 6, the illustration of a blood supply mechanism 10, a casing 30, a back lid 86, a back lid seal 87 and the like is omitted.

1. Core Position Adjusting Member 6

The blood pump 2 according to the embodiment 2 basically has substantially the same configuration as the blood pump 1 according to the embodiment 1. However, the blood pump 2 according to the embodiment 2 differs from the blood pump 1 according to the embodiment 1 with respect to a point that the blood pump 2 further includes a core position adjusting member 6.

That is, as shown in FIG. 5 and FIG. 6, compared to the blood pump 1 according to the embodiment 1, the blood pump 2 according to the embodiment 2 further includes the core position adjusting member 6 where the blood pump 2 has a screw portion 7 on which threads 7a are formed. The screw portion 7 engages with a suitable portion of a stator 110 due to the rotation of the screw portion 7 so that a core 114 is moved in the direction parallel to the z axis.

For example, the core position adjusting member 6 shown in FIG. 5 and FIG. 6 is formed into a circular cylindrical shape with the z axis set as the center of a circle. The core position adjusting member 6 engages with the core 114. When the core position adjusting member 6 is rotated with the z axis set as the center, due to an action of the screw portion 7, the core position adjusting member 6 moves in the direction parallel to the z axis. Since the core position adjusting member 6 engages with a suitable portion (for example, the core 114) of the stator 110, the core 114 also moves in the direction parallel to the z axis along with the movement of the core position adjusting member 6.

In this manner, according to the blood pump 2 in the embodiment 2, by changing a rotation angle of the screw portion 7 of the core position adjusting member 6, the position of the stator 110 (in other words, the position of the core 114) can be adjusted by moving the position of the stator 110 little by little in the direction parallel to the z axis. That is, the displacement of a rotation angle of the core position adjustment member 6 can be converted into the displacement of the stator 110 (in other words the core 114) in the direction parallel to the z axis by way of the screw portion 7 of the core position adjustment member 6. Accordingly, with the use of such a core position adjusting member 6, the position of the stator 110 (in other words, the core 114) can be adjusted with high accuracy and efficiently and, eventually, a given pressure can be also adjusted with high accuracy and efficiently. As a result, a force by which the rotary side slide member is pressed to the fixed side slide member (pressing force) can be adjusted with high accuracy and efficiently.

2. Adjustment Ring 60

In the above-mentioned blood pump 2 according to the embodiment 2, it is preferable that the core position adjustment member 6 is formed of an adjustment ring 60 having a circular cylindrical shape with the z axis set as the center of a circle.

As shown in FIG. 5 and FIG. 6, the adjustment ring 60 is disposed outside the core 114. In other words, the core 114 is disposed inside of the adjustment ring 60.

A lower peripheral edge 63 of the adjustment ring 60 protrudes from a lower end portion 117 of the core 114 in the +z direction. Accordingly, in performing the core position adjustment, the core 114 does not obstruct the adjustment ring 60 and hence, an adjuster can grip the lower peripheral edge 63 of the circular sleeve whereby the adjustment ring 60 can be easily rotated.

First threads 66 which form the screw portion 7 are formed on an outer surface of the adjustment ring 60.

An engaging protruding portion 65 is formed on an upper peripheral edge 64 of the adjustment ring 60. The engaging protruding portion 65 may have any shape provided that the engaging protruding portion 65 is formed in a shape so as to move the core 114 together with the adjustment ring 60 when the adjustment ring 60 moves in the +z direction. For example, as shown in FIG. 6, the engaging protruding portion 65 may be formed in the shape where the engaging protruding portion 65 protrudes towards the inside (the core 114 side) such that the engaging protruding portion 65 is continually bent from the circular cylindrical portion of the adjustment ring 60 (hocked shape) in the vicinity of the upper peripheral edge 64 of the adjustment ring 60.

On the other hand, a side wall portion 26 protruding in a circular cylindrical shape in the +z direction from an outer edge of the pedestal portion 22 is formed on the base body 20 (see FIG. 5). Second threads 28 are formed on an inner wall 27 of the side wall portion 26 (see FIG. 6).

The first threads 66 and the second threads 28 threadedly engage with each other, and the engaging protruding portion 65 of the adjustment ring 60 is brought into contact with an upper end portion 116 of the core 114.

With the above-mentioned configuration, the core 114 which is brought into contact with the engaging protruding portion 65 can be moved along the z axis due to the movement of the engaging protruding portion 65 along the z axis caused by rotation of the adjustment ring 60.

In this manner, the first threads 66 formed on the outer surface of the adjustment ring 60 and the second threads 28 formed on the inner wall 27 of the side wall portion 26 of the base body 20 threadedly engage with each other. Accordingly, by rotating the adjustment ring 60 by applying a force to the adjustment ring 60 in the circumferential direction of the adjustment ring 60, the engaging protruding portion 65 of the adjustment ring 60 can be moved along the z axis. Due to the movement of the engaging protruding portion 65 along the z axis, the core 114 which is brought into contact with the engaging protruding portion 65 can be also moved along the z axis. In this manner, the position of the core 114 can be moved along the z axis by rotating the adjustment ring 60.

Particularly, a rotating portion of the adjustment ring 60 has a large diameter compared to a core position adjustment member formed of a feeding screw or the like. Accordingly, even when a periphery of the adjustment ring 60 is largely moved in the circumferential direction, the displacement of a rotation angle brought about by such movement of the adjustment ring 60 is relatively small. Further, the adjustment ring 60 has a circular cylindrical shape and hence, first threads 66 can be easily formed on an outer surface of the adjustment ring 60 at a relatively narrow pitch with high accuracy. Further, with the introduction of the adjustment ring 60 as the core position adjustment member 6, it is possible to provide a mechanism where even when the adjustment ring 60 is moved in the circumferential direction with a large operation amount, such a large operation amount is converted into a small moving amount of the adjustment ring in the direction parallel to the z axis.

Accordingly, with the provision of the adjustment ring 60 of the embodiment 2, the position of the core 114 can be adjusted with high accuracy and hence, it is possible to adjust a given pressure with high accuracy and efficiently. As a result, a force (pressing force) by which the rotary side slide member presses the fixed side slide member can be adjusted with high accuracy and efficiently.

To increase a torque of the motor 100 of the blood pump there is a demand for narrowing as much as possible a so-called air gap G between the stator 110 and the rotor 120 (for example, the gap G between the inner peripheral wall 115 of the core and the outer peripheral surface 123 of the permeant magnet 122 in the inner-rotor-type motor, see FIG. 6). However, there is a demand that the narrower the air gap G, the more accurate the positional adjustment (along with the direction parallel to the z axis) of the core becomes necessary for adjusting a magnitude of the given pressure.

Even under such a state where the strict positional adjustment is demanded due to narrowing of the air gap G, by introducing the adjustment ring 60 in the embodiment 2, the blood pump 2 according to the embodiment 2 can acquire both the enhancement of the torque of the motor and the accurate and efficient adjustment of a given pressure.

3. Stator Fixed Ring 80

Since the core 114 is attracted by the permeant magnet 122, the core 114 itself receives a force in the −z direction due to a reaction (see FIG. 3A and FIG. 3B). Accordingly, the upper end portion 116 of the core 114 is brought into contact with the engaging protruding portion 65 of the adjustment ring 60 in the −z direction by pushing.

Accordingly, even if the engaging protruding portion 65 is slightly moved in the −z direction, the upper end portion 116 of the core 114 also moves following such movement of the engaging protruding portion 65.

However, in the above-mentioned blood pump 2 according to the embodiment 2, it is preferable that the blood pump 2 further include a stator fixing ring 80 fitted on an inner side of the adjustment ring 60 such that the stator fixing ring 80 is brought into contact with the lower end portion 117 of the core 114 (see FIG. 6).

With such a configuration, the core 114 is sandwiched between the stator fixing ring 80 and the engaging protruding portion 65 of the adjustment ring 60. Accordingly, the position of the core 114 is further firmly fixed and hence, there is no possibility that the core 114 is easily displaced toward the z axis direction.

4. Complimentary Description

The blood pump 2 according to the embodiment 2 has substantially the same configuration as the blood pump 1 according to the embodiment 1 except for a point that the blood pump 2 further includes the core position adjusting member 6, a point that the blood pump 2 includes the adjustment ring 60, and a point that the blood pump 2 includes the stator fixing ring 80. The blood pump 2 according to the embodiment 2 has substantially the same configuration as the blood pump 2 according to the embodiment 1 except for the above-mentioned points. Accordingly, the blood pump 2 according to the embodiment 2 directly acquires the corresponding advantageous effects found amongst all advantageous effects which the blood pump 1 according to the embodiment 1 acquires.

In the description of the embodiment 1, the description has been made with respect to the case where the blood pump 1 according to the embodiment 1 is applied to the artificial heart system 5. However, the blood pump 2 according to the embodiment 2 can be also applied to a ventricular assist system in the same manner as the embodiment 1. Also in this case, it is possible to acquire advantageous effects substantially equal to advantageous effects described in the description of the embodiment 1.

Embodiment 3

Figure 7:
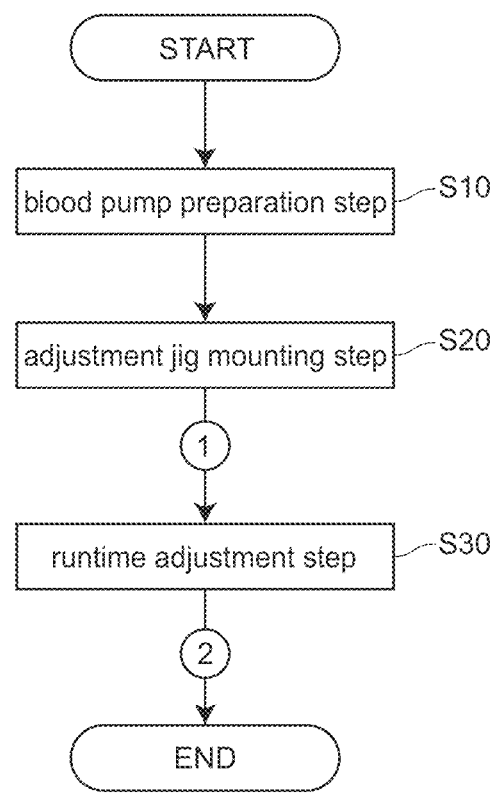
FIG. 7 is a flowchart for describing a blood pump adjusting method according to an embodiment 3.
Figure 8:
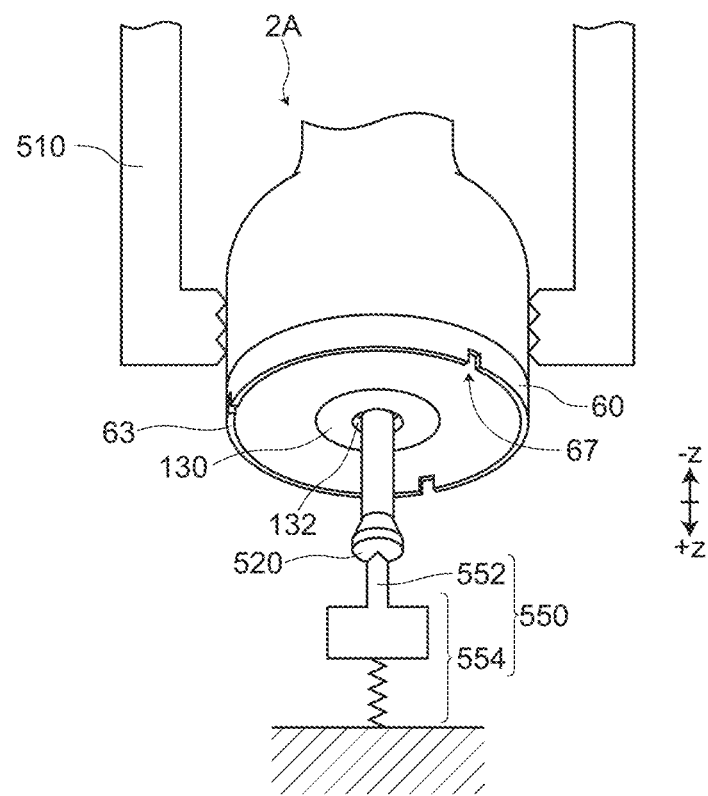
FIG. 8 is a view for describing the blood pump adjusting method according to the embodiment 3.
Figure 9:
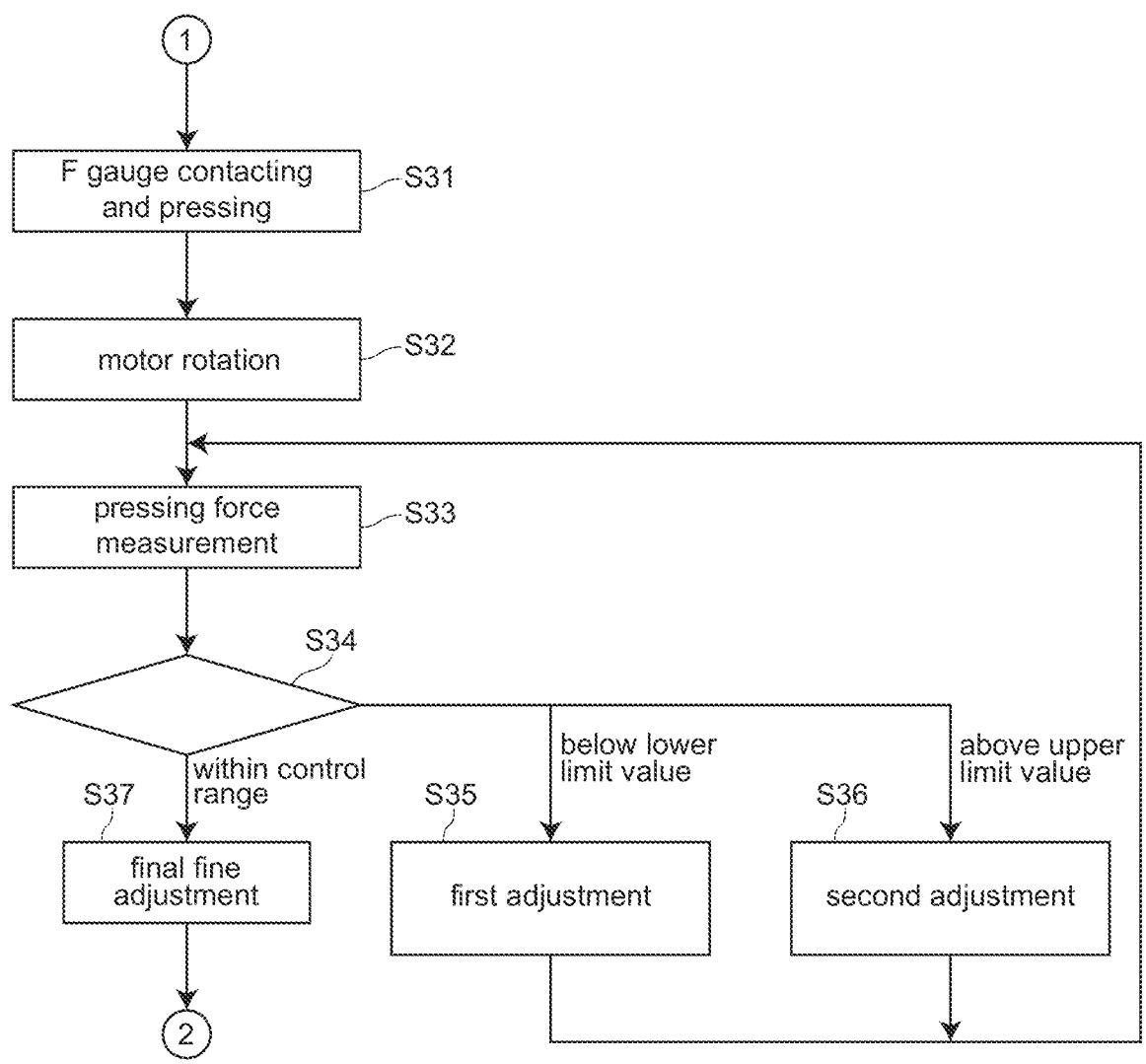
FIG. 9 is a flowchart of a runtime adjustment step S30 for describing the blood pump adjusting method according to the embodiment 3.

FIG. 7 is a flowchart for describing a blood pump adjusting method according to an embodiment 3. FIG. 8 is a view for describing the blood pump adjusting method according to the embodiment 3. To be more specific, FIG. 8 is a schematic view for describing an adjustment jig mounting step S20(described later) and the runtime adjustment step S30 (described later). FIG. 8 is a view showing a stage where a spin top 520 is being inserted into a hollow portion 132 of the shaft 130, and is also a view where the spin top 520 is not completely inserted into the hollow portion 132. FIG. 9 is a flowchart of a runtime adjustment step S30 for describing the blood pump adjusting method according to the embodiment 3.

Hereinafter, the blood pump adjusting method according to the embodiment 3 is described on the premise of the case where the blood pump 2 according to the embodiment 2 is used.

1. Blood Pump Adjusting Method According to the Embodiment 3

As shown in FIG. 7, the blood pump adjusting method according to the embodiment 3 includes, in the blood pump adjusting method according to the embodiment 2, the blood pump preparation step S10, an adjustment jig mounting step S20, and the runtime adjustment step S30.

(1) Blood Pump Preparation Step S10

In the blood pump preparation step S10, the adjustment state blood pump 2A is prepared in the state where at least a portion of the shaft 130 on the +z direction side is exposed.

For example, as shown in FIG. 5 and FIG. 8, the back lid 86 and the back lid seal 87 of the blood pump 2 are removed from the body of the blood pump 2 so as to expose at least a portion of the shaft 130 on the +z direction side. Hexagon socket set screws 68 are also removed so as to bring the adjustment ring 60 in a rotatable state.

(2) Adjustment Jig Mounting Step S20

The adjustment jig mounting step S20 has: a step of holding the adjustment state blood pump 2A by a blood pump holder 510; and a step of connecting a controller 230 for controlling the adjustment state blood pump 2A to the adjustment state blood pump 2A (not shown in FIG. 8).

To be in more detail, as shown in FIG. 8, the body of the adjustment state blood pump 2A is held by the blood pump holder 510 using a suitable method. Accordingly, it is possible to prevent the body(the base body 20, casing 30 and the like) of the adjustment state blood pump 2A from moving in the direction parallel to the z axis, the direction perpendicular to the z axis, the rotational direction and the like. The controller 230 (not shown in FIG. 8) for controlling the adjustment state blood pump is connected to the adjustment state blood pump 2A, and a state is prepared where the adjustment state blood pump 2A can be operated under a predetermined condition. An externally mountable jig through which a liquid flows may be mounted on the inflow port 32 and the outflow port 34 of the pump chamber R respectively.

In the case where the shaft 130 has a hollow portion 132 on a +z direction side, as shown in FIG. 8, a step of embedding the spin top (auxiliary jig) 520 into the hollow portion 132 may be also performed. By performing such a step, it is possible to bring a probe 552 of a force gauge 550 (described later) into contact with the center of rotation of the shaft 130.

(3) Runtime Adjustment Step S30

The runtime adjustment step S30 is a step of adjusting the blood pump while actually operating the blood pump. As shown in FIG. 9, the runtime adjustment step S30 has: an F gauge contacting and pressing step S31; a motor rotation step S32; a pressing force measurement step S33; a determination step S34, a first adjustment step S35; and a second adjustment step S36.

(i) In the F gauge contacting and pressing step S31, the probe 552 of the force gauge 550 is brought into contact with the center of rotation (z axis) of the shaft 130 from a +z direction side (lower side) of the shaft 130 so that the shaft 130 is pressed toward the −z direction (see also FIG. 8).

(ii) In the motor rotation step S32, the motor 100 of the adjustment state blood pump 2A is rotated under a predetermined condition. For example, the motor 100 of the adjustment state blood pump 2A is rotated by suitably selecting a rotational speed in conformity with the specification of the blood pump, an actual use condition or the like of the blood pump.

(iii) In the pressing force measurement step S33, a magnitude of a force obtained by way of the probe 552 is read as a value by the force gauge 550, and the value is measured as a pressing force.

(iv) As described previously, a pressing force on the seal slide surface of the mechanical seal should be controlled so as to have a value which falls within an appropriate range. This appropriate range from an upper limit value to a lower limit value of the pressing force is defined as "control range". In determination step S34, it is determined whether or not a measured pressing force falls within the above-mentioned control range, whether or not the measured pressing force is below the lower limit value of the control range, and whether or not the measured pressing force is above the upper limit value of the control range or the like.

(v) First Adjustment Step S35

When it is determined that the measured pressing force is below the lower limit value of the predetermined control range, first adjustment step S35 is performed. In first adjustment step S35, the adjustment is made by moving the core 114 in the +z direction (downward direction) by rotating the adjustment ring 60 in the first rotational direction.

In performing the adjustment, an adjustment ring rotation jig (not shown in the drawings) may be used. The adjustment ring rotation jig grips the lower peripheral edge 63 of the adjustment ring 60 in any form. Then, a force is applied to the adjustment ring 60 in a circumferential direction by the adjustment ring rotation jig so that adjustment ring 60 can be rotated. Accordingly, the desired adjustment can be performed.

(vi) Second Adjustment Step S36

When it is determined that a measured pressing force is above the upper limit value of the predetermined control range, second adjustment step S36 is performed. In second adjustment step S36, the adjustment is made by moving the core 114 in the −z direction (upward direction) by rotating the adjustment ring 60 in the second rotational direction opposite to the first rotational direction. The specific method is substantially the same as the specific method performed in the above-mentioned first adjustment step S35.

2. Advantageous Effects Acquired by Blood Pump Adjustment Method According to Embodiment 3

In the case where the blood pump adjusting method according to the embodiment 3 is not used, it is necessary to repeatedly perform the following cumbersome operation. The cumbersome operation includes: an operation of measuring an actual pressing force by running an existing blood pump; an operation of disassembling the blood pump; an operation of adjusting parts of the blood pump relevant to a pressing force; an operation of assembling the blood pump; and an operation of confirming whether or not a pressing force is corrected by running the blood pump again.

On the other hand, according to the blood pump adjusting method of the embodiment 3, by performing first adjustment step S35 and second adjustment step S36 while measuring an actual pressing force in pressing force measurement step S33 using an existing blood pump, the adjustment can be performed such that the actual pressing force takes a value which falls within an appropriate range.

Accordingly, a force (pressing force) which presses the rotary side slide member to the fixed side slide member can be adjusted with high accuracy and efficiently.

3. Complementary Description (1) After first adjustment step S35 and second adjustment step S36 described above are performed, the processing may return to pressing force measurement step S33 again, and pressing force measurement step S33, determination step S34, first adjustment step S35, or second adjustment step S36 may be repeated.

(2) In addition to the above-mentioned steps and sub steps, the following steps and sub steps may be further performed.

When it is determined that a measured pressing force falls within a predetermined control range, final fine adjustment step S37 may be performed. Final fine adjustment step S37 is a step of making an actual pressing force closer to a center value of the control range. To be more specific, when pressing force measurement step S33 is performed and it is determined that the actual pressing force is below the center value, the adjustment ring 60 is rotated in the first rotational direction. When it is determined that the actual pressing force is above the center value, the adjustment ring 60 is rotated in the second rotational direction. It is preferable that a displacement of an angle that the adjustment ring 60 is rotated (rotating angle) be smaller than displacements of angles in first adjustment step S35 and second adjustment step S36. This is because that the more accurate adjustment can be realized.

After final fine adjustment step S37 is performed, the side wall portion 26 of the base body 20 and the adjustment ring 60 are made to engage with each other by the hexagon socket set screws 68 so as to fix the adjustment ring 60 such that the adjustment ring 60 is not rotated relative to the base body 20. Then, the adjustment ring 60 and the side wall portion 26 may be sealed by a resin or the like thus completely fixing the adjustment ring 60.

After the adjustment ring 60 is fixed, the blood pump 2 is assembled by fitting the back lid seal 87 and the back lid 86 on the base body 20 from the +z direction side.

EXAMPLE

An example of the blood pump obtained by carrying out the present invention is described hereinafter.

Figure 10:
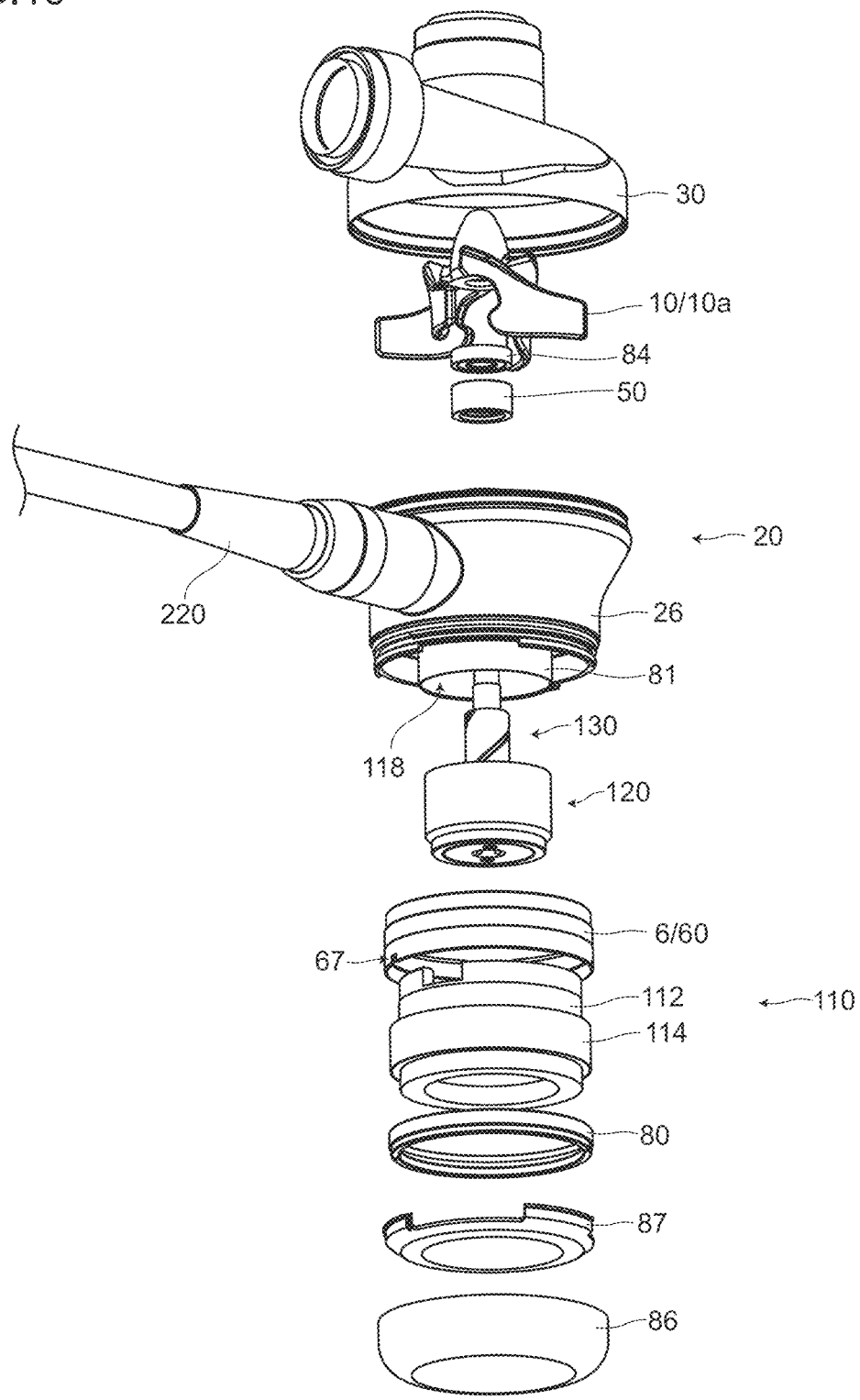
FIG. 10 is an exploded view for describing a blood pump according to an example.
Figure 11:
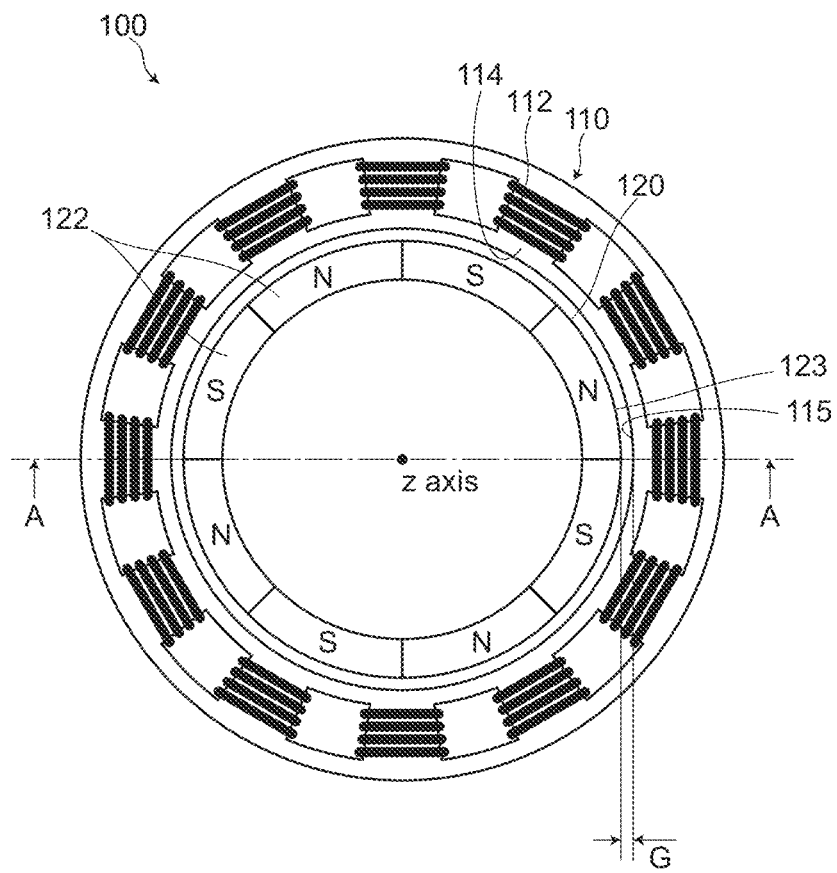
FIG. 11 is a cross-sectional view for describing the blood pump according to the example.

FIG. 10 is an exploded view for describing the blood pump according to the example. FIG. 10 is a perspective view as viewed from an oblique downward position. Accordingly, the fixed side slide member 40, an upper surface of the pedestal portion 22 and the like do not appear. FIG. 11 is a cross-sectional view for describing the blood pump according to the example. FIG. 11 is a cross-sectional view of the motor 100 taken along a plane perpendicular to the z axis. The shaft 130 is not shown in the drawing.

The blood pump 2 according to the embodiment 2 is used as the blood pump according to the example (see FIG. 10).

(1) Summary of Blood Pump According to Example

A centrifugal-type impeller 10a is adopted as the blood supply mechanism 10.

So-called seat ring is adopted as the fixed side slide member 40. The seat ring (fixed side slide member 40) is made of ceramic. For example, the seat ring is made of silicon carbide (SiC). The seat ring is fixed to the base body 20. The seat ring is fixed with respect to the rotational direction (radial direction) using the z axis as a center, and also is fixed with respect to the direction (thrust direction) along the z axis. The seat ring also functions as a thrust bearing which receives weights of the shaft 130, the impeller 10a, the rotary side slide member 50 and the like.

A so-called seal ring is adopted as the rotary side slide member 50. In this example, the seal ring (rotary side slide member 50) is made of carbon.

The cushion ring 84 is interposed between the impeller 10a and the seal ring (rotary side slide member 50). The cushion ring 84 is made of silicon rubber.

By interposing the cushion ring 84 between the blood supply mechanism 10 and the rotary side slide member 50, the cushion ring 84 functions as a damper. Accordingly, the cushion ring 84 can absorb an impact transmitted from both the blood supply mechanism 10 and the rotary side slide member 50.

A so-called inner-rotor-type blushless DC motor is adopted as the motor 100.

In the blood pump according to the example, the motor 100 is an inner-rotor-type motor, and a rotor housing space 118 capable of housing the rotor 120 is formed inside of the motor 100 close to a z axis of the stator 110. The rotor 120 is housed in the rotor housing space 118 in a state where the rotor 120 is movable along the z axis.

In the case where the motor 100 is an inner-rotor-type motor, compared to the case where the motor 100 is an outer-rotor-type motor, the permanent magnet 122 of the rotor 120 is disposed at a location close to the rotary axis (z axis). That is, a point on which a given pressure acts is disposed at the location close to the rotary axis. Accordingly, a given pressure transmitted to the fixed side slide member 40 by way of the shaft 130 can be transmitted in a stable state where irregularities in the direction of a force, a magnitude of the force and the like are relatively small. As a result, such a motor contributes to accurate applying of a pressing force to the seal slide surface of the mechanical seal.

As shown in FIG. 11, the motor 100 adopts, as the permanent magnet 122 of the rotor 120, the permanent magnet having the configuration where the number of poles is 8 consisting of 4 N poles and 4 S poles. The stator 110 has 12 cores 114 and, the coil 112 is wound around the respective cores 114.

A height (a length in the direction parallel to the z axis) of the core 114 is set to 6 to 10 mm. A height (a length in the direction parallel to the z axis) of the permanent magnet 122 is set to 8 to 12 mm.

In this example, it is preferable that an air gap G formed between the inner peripheral wall 115 of the core 114 and the outer peripheral surface 123 of the permanent magnet 122 be set to a value which falls within a range of from 0.7 mm to 1.3 mm.

By setting the value of the air gap G within such a range, it is possible to provide a blood pump having a small volume and a small weight, and can easily adjust a pressing force.

A liquid flow passage 70 is formed in the blood pump. The liquid flow passage 70 is surrounded by a surface which faces the +z direction out of surfaces which form the seal ring (rotary side slide member 50), an inner peripheral surface of the first insertion hole 44 of the seat ring (fixed side slide member 40) and any surface which forms the shaft 130 (see FIG. 2, also see FIG. 5). A cooling liquid for cooling the motor 100, the shaft 130 and the like passes through the liquid flow passage 70. The seal ring (rotary side slide member 50) receives a force in the −z direction due to a liquid pressure of such cooling liquid.

Further, to prevent the cooling liquid from flowing into portions other than portions which require cooling, a stator partition wall 81 (see FIG. 3A, FIG. 3B and FIG. 6), the back lid seal 87(see FIG. 1 and FIG. 5) and the like are provided. The rotor 120 is surrounded by a rotor case 124 made of titanium so that the inside of the rotor 120 is protected (see FIG. 3A, FIG. 3B and FIG. 6).

2) Shift Amount of Center CM of Permanent Magnet with Respect to Center CC of Core In the blood pump, it is preferable that a shift amount SFT of the center CM of the permanent magnet with respect to the center of the core fall within a range of from 0.1 mm to 1.0 mm.

It is more preferable that the shift amount SFT fall within a range of from 0.2 mm to 1.0 mm inclusive. By setting the shift amount to a value which falls in such a range, it is possible to provide the blood pump having a smaller volume and a smaller weight compared to the conventional blood pump while ensuring a necessary and sufficient given pressure.

It is still more preferable that the shift amount SFT fall within a range of from 0.3 mm to 0.6 mm inclusive.

Figure 12:
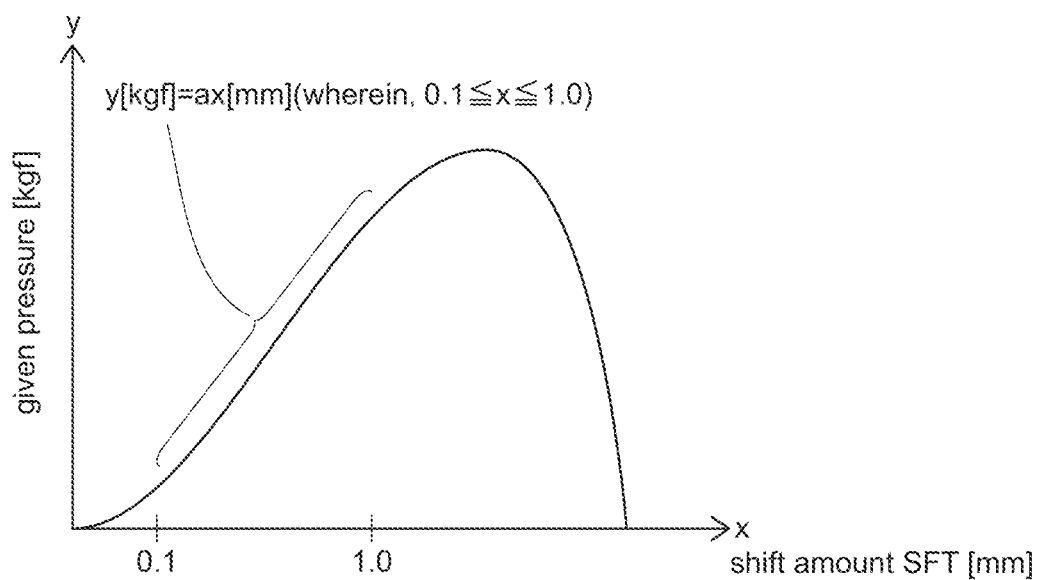
FIG. 12 is a graph showing a relationship between a shift amount SFT of the center CM of a permanent magnet with respect to the center CC of a core in the blood pump according to the example and a given pressure which contributes to a pressing force on a seal slide surface of a mechanical seal.

FIG. 12 is a graph showing a relationship between a shift amount SFT of the center CM of the permanent magnet with respect to the center CC of the core in the blood pump according to the example and a given pressure which contributes to a pressing force on the seal slide surface.

In general, there is a possibility that a relationship between a shift amount SFT and a given pressure changes. However, so long as the shift amount SFT is limited to a value which falls within a specified zone, it is regarded that a linear relationship expressed by a linear function exists between a shift amount SFT and a given pressure (see FIG. 12).

For example, in the blood pump according to the example, assuming a shift amount SFT as x[mm] and a given pressure as y[kgf], it is regarded that a relationship between the shift amount SFT and the given pressure is expressed by a linear function of y=ax (wherein, $0.1 \leq x \leq 1.0$).

Accordingly, in the adjustment of a given pressure, it is preferable to perform the positional adjustment of the core 114 within a specified zone (in this example, $0.1 \leq x \leq 1.0$). This is because a given pressure can be linearly changed by adjusting a rotational angle of the adjustment ring 60. As a result, it is possible to impart a pressing force with high accuracy.

(3) Adjustment Ring 60

The blood pump according to the example adopts the adjustment ring 60 as the core position adjusting member 6.

A diameter of the adjustment ring 60 is set to approximately 30 to 60 mm.

The threads 7a of screw portion 7 of the adjustment ring 60 are formed at a pitch which allows the adjustment ring 60 to be displaced in the direction parallel to the z axis by approximately 0.2 to 0.3 mm each time the adjustment ring 60 having a circular cylindrical shape is rotated by one turn (the rotation of 360°).

A notch 67 is formed in the lower peripheral edge 63 of the adjustment ring 60 (see FIG. 10 and FIG. 8). By forming such a notch 67, it is possible to make an adjustment ring rotation jig (not shown in the drawings) provided for rotating the adjustment ring 60 easily engage with the adjustment ring 60 by fitting engagement. Accordingly, a slippage minimally occurs at the time of making the adjustment ring rotation jig engage with the adjustment ring 60 and hence, the more accurate adjustment can be realized.

The blood pump according to the example further includes the stator fixing ring 80.

(4) In the blood pump according to the example, a given pressure in the +z direction applied from the rotary side slide member 50 to the fixed side slide member 40 by way of the rotor 120 and the shaft 130 is set by taking into account a liquid pressure of a cooling liquid which passes through the liquid flow passage 70 when the blood pump is operated.

In the blood pump, there may be the case where a cooling liquid (for example, cooling water) is made to circulate in the liquid flow passage so as to cool the whole motor including the shaft, the fixed side slide member, the rotary side slide member or the like. For reference purposes, a magnitude of a liquid pressure of the cooling liquid may change corresponding to an operation state of the blood pump. However, as viewed in general, the magnitude of the liquid pressure is set to a value which falls within an appropriate range.

A liquid pressure of the cooling liquid acts as a force in the direction that the rotary side slide member 50 is separated from the fixed side slide member 40 by pulling (a force in the −z direction). Accordingly, a given pressure applied by the adjustment ring 60 is set and adjusted by taking into account the liquid pressure of the cooling liquid. That is, with respect to a pressing force on the seal slide surface of the mechanical seal, an amount of the liquid pressure of a cooling liquid is cancelled as a force on an opposite side and hence, a force to which such an amount of the liquid pressure is added is set as the given pressure.

As described above, by operating the blood pump according to the present invention, it can be confirmed that, unlike the conventional blood pumps, the rotary side slide member can be pressed to the fixed side slide member without particularly providing the additional members (the first permanent magnet and the second permanent magnet).

Although the present invention has been described based on the above-mentioned embodiments heretofore, the present invention is not limited to the above-mentioned embodiments.

The present invention can be carried out without departing from the gist of the present invention, for example, the following modifications are also conceivable.

(1) The numbers, the materials, the shapes, the positions, the sizes, and the like of the constitutional elements described in the above-mentioned respective embodiments are provided only for an exemplifying purpose, and these can be changed within ranges where advantageous effects of the present invention are not impaired.

(2) In the above-mentioned respective embodiments, the description has been made by estimating the case where the motor 100 is an inner-rotor-type motor. However, the present invention is not limited to such a case. For example, as the motor 100, an outer-rotor-type motor may be adopted. In this case, as viewed in the radial direction about the rotary axis, the stator (the core and the coils) is disposed on an inner side of the motor 100 and the rotor having the permanent magnet is disposed on an outer side of the motor.

(3) In the above-mentioned respective embodiments, for example, shims 400 may be used for adjusting the position of the core.

Figure 13:
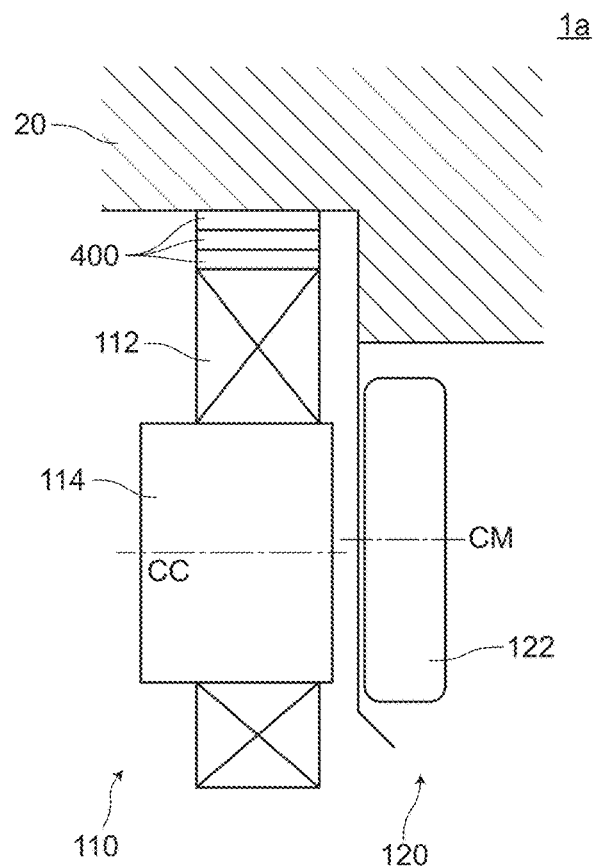

FIG. 13 is a cross-sectional view of a main part of a blood pump 1a according to a modification 1 for describing the blood pump 1a. The shim 400 is a member having a relatively thin thickness and is used as a spacer. As shown in FIG. 13, a required number of shims 400 are inserted between the base body 20 and the stator 110 (including the core 114 and the coils 112) in a stacked manner. By adjusting the number of stacked shims 400, the position of the center CC of the core can be adjusted relative to the position of the center CM of the permanent magnet.

(4) In the above-mentioned embodiment 2 and embodiment 3, the description has been made with respect to the case where the adjustment ring 60 is used as the core position adjusting member 6. However, the present invention is not limited to such a case. For example, a feed screw 6a may be adopted as the core position adjusting member 6.

Figure 14:
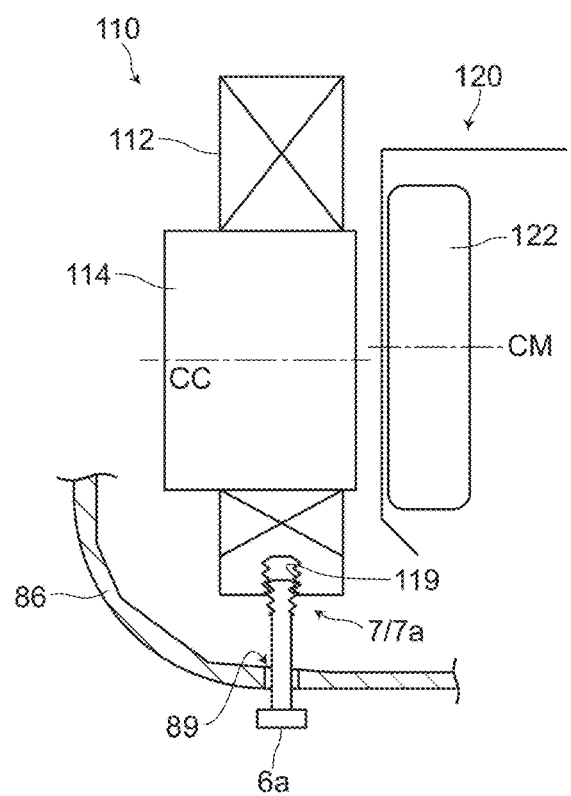
Figure 15:
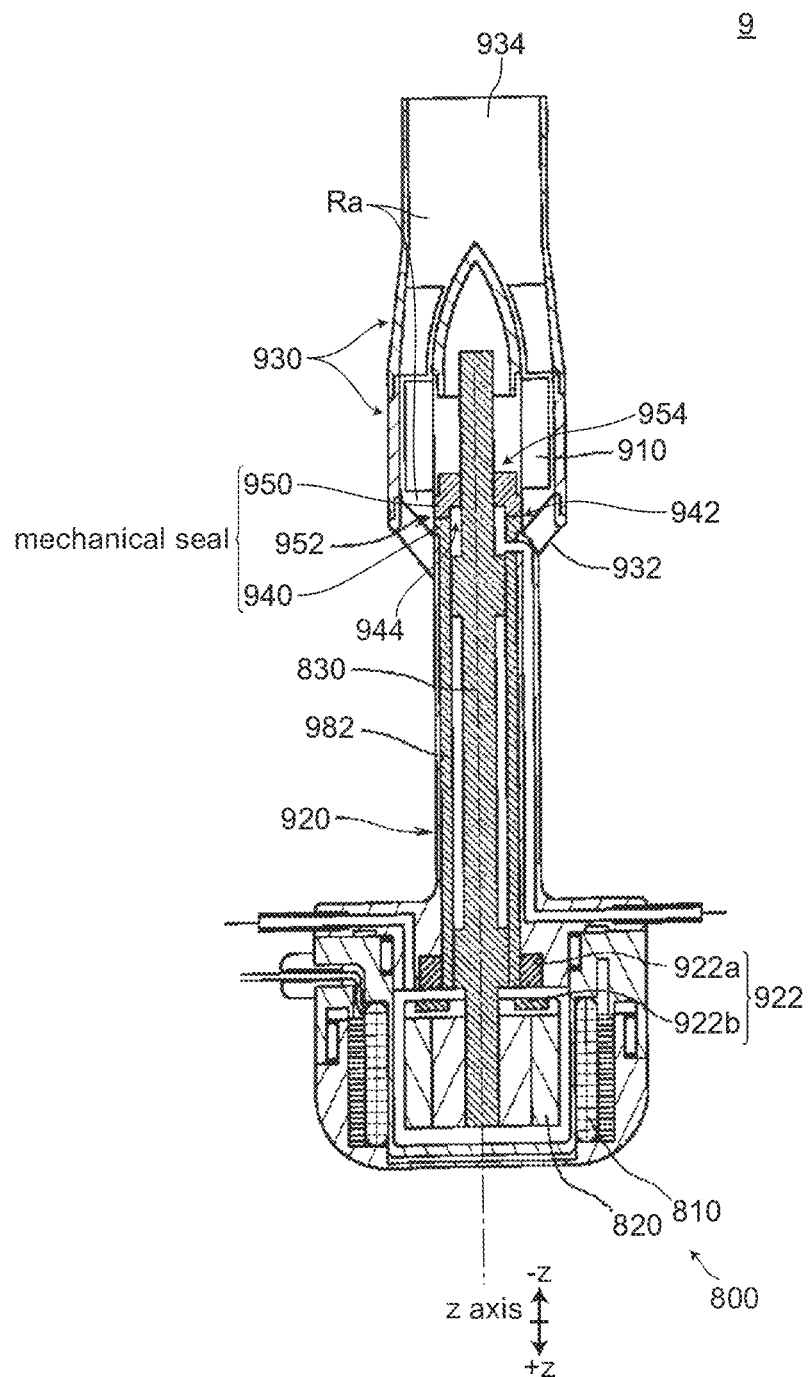
FIG. 15 is a cross-sectional view of a conventional blood pump 9 for describing the blood pump 9.

FIG. 14 is a cross-sectional view of a main part of a blood pump 2a according to a modification 2 for describing the blood pump 2a. For example, as shown in FIG. 14, female threads 119 are formed in a suitable portion of the stator 110 (including the core 114 and the coils 112). The feed screw 6a having a screw portion 7 on a distal end thereof is made to pass through a loose hole 89 formed in the back lid 86, and threads 7a of the screw portion 7 are threadedly engaged with the above-mentioned female threads 119.

With such a configuration, the stator 110 can be moved in the direction parallel to the z axis by rotating the feed screw 6a. As a result, the core 114 can be moved in the direction parallel to the z axis.

(5) In the blood pump adjusting method according to the above-mentioned embodiment 3, motor rotation step S32 is performed after F gauge contacting and pressing step S31 is performed. However, the present invention is not limited to such a case. By changing the order of these steps, the F gauge contacting and pressing step S31 may be performed after motor rotation step S32 is performed. In this case, the measurement, recording or the like of z by a force gauge can be performed in a state where the rotation of the motor is stable.

The invention claimed is:

1. A blood pump for causing blood to flow into a pump chamber, flow out from the pump chamber, and flow into the inside of a body of a user by a blood supply mechanism housed in the pump chamber, the blood pump comprising:
the blood supply mechanism connected to one end of a shaft and capable of moving a liquid due to rotation thereof;
a motor having a stator and a rotor, having the shaft connected to the rotor, and imparting rotational energy to the blood supply mechanism by way of the shaft;
a base body having a pedestal portion which partitions the blood pump into a pump chamber side and a rotor side which is a side opposite to the pump chamber, wherein a through hole which allows the shaft to pass therethrough is formed in the base body at a position close to a center of the pedestal portion;
a casing fitted into the base body thus forming the pump chamber together with the base body;
a fixed side slide member having a first slide surface, wherein a first insertion hole which allows the shaft to pass therethrough is formed in the fixed side slide member, and the fixed side slide member is fixed to the base body at a position corresponding to the through hole; and
a rotary side slide member having a second slide surface, wherein a second insertion hole which allows the shaft to pass therethrough is formed in the rotary side slide member, the shaft is fitted into the second insertion hole in a state where the shaft is interposed between the fixed side slide member and the blood supply mechanism, and the second slide surface is slidable on the first slide surface in a contact manner with the first slide surface by rotating together with the blood supply mechanism and the shaft, wherein
the stator has a core around which a coil is wound,
the rotor has a permanent magnet disposed so as to opposedly face a peripheral wall of the core, wherein an N pole and an S pole are alternately arranged along a circumferential direction that the rotor rotates,
assuming a rotary axis of the rotor as a z axis, a direction along the z axis extending from the pump chamber side to the rotor side as a +z direction, and a direction opposite to the +z direction as a −z direction,
the stator is fixed to the base body,
the rotor is movable relative to the stator along a direction parallel to the z axis,
a center of the core in the direction parallel to the z axis is located at a position shifted on a more +z direction side than a center of the permanent magnet in the direction parallel to the z axis, and
the blood pump further comprises a core position adjusting member having a screw portion on which threads are formed, the core position adjusting member being capable of moving the core in the direction parallel to the z axis while being engaging with any portion of the stator of the screw portion.

2. The blood pump according to claim 1, wherein
the core position adjusting member is an adjustment ring having a circular cylindrical shape with the z axis set as a center of a circle,
the core is disposed inside of the adjustment ring, and a lower peripheral edge of the adjustment ring protrudes from a lower end portion of the core in the +z direction,
first threads which form the screw portion is formed on an outer surface of the adjustment ring, and an engaging protruding portion is formed on an upper peripheral edge of the adjustment ring,
a side wall portion protruding in a circular cylindrical shape in the +z direction from an outer edge of the pedestal portion is formed on the base body, and second threads are formed on an inner wall of the side wall portion,
the first threads and the second threads threadedly engage with each other, and the engaging protruding portion of the adjustment ring is brought into contact with an upper end portion of the core, and
the core which is brought into contact with the engaging protruding portion is configured to be movable along the z axis due to the movement of the engaging protruding portion along the z axis caused by rotation of the adjustment ring.

3. The blood pump according to claim 2, further comprising a stator fixing ring fitted on an inner side of the adjustment ring such that the stator fixing ring is brought into contact with a lower end portion of the core.

4. A blood pump adjusting method for adjusting a blood pump which causes blood to flow into a pump chamber, flow out from the pump chamber, and flow into the inside of a body of a user by a blood supply mechanism housed in the pump chamber,
the blood pump comprising:
the blood supply mechanism connected to one end of a shaft and capable of moving a liquid due to rotation thereof;
a motor having a stator and a rotor, having the shaft connected to the rotor, and imparting rotational energy to the blood supply mechanism by way of the shaft;
a base body having a pedestal portion which partitions the blood pump into a pump chamber side and a rotor side which is a side opposite to the pump chamber, wherein a through hole which allows the shaft to pass therethrough is formed in the base body at a position close to a center of the pedestal portion;
a casing fitted into the base body thus forming the pump chamber together with the base body;
a fixed side slide member having a first slide surface, wherein a first insertion hole which allows the shaft to pass therethrough is formed in the fixed side slide member, and the fixed side slide member is fixed to the base body at a position corresponding to the through hole; and
a rotary side slide member having a second slide surface, wherein a second insertion hole which allows the shaft to pass therethrough is formed in the rotary side slide member, the shaft is fitted into the second insertion hole in a state where the shaft is interposed between the fixed side slide member and the blood supply mechanism, and the second slide surface is slidable on the first slide surface in a contact manner with the first slide surface by rotating together with the blood supply mechanism and the shaft, wherein
the stator has a core around which a coil is wound,
the rotor has a permanent magnet disposed so as to opposedly face a peripheral wall of the core, wherein an N pole and an S pole are alternately arranged along a circumferential direction that the rotor rotates,
assuming a rotary axis of the rotor as a z axis, a direction along the z axis extending from the pump chamber side to the rotor side as a +z direction, and a direction opposite to the +z direction as a −z direction,
the stator is fixed to the base body,
the rotor is movable relative to the stator along a direction parallel to the z axis,
a center of the core in the direction parallel to the z axis is located at a position shifted on a more +z direction side than a center of the permanent magnet in the direction parallel to the z axis,
the blood pump further comprises a core position adjusting member having a screw portion on which threads are formed, the core position adjusting member being capable of moving the core in the direction parallel to the z axis while being engaging with any portion of the stator due to rotation of the screw portion,
the core position adjusting member is an adjustment ring having a circular cylindrical shape with the z axis set as a center of a circle,
the core is disposed inside of the adjustment ring, and a lower peripheral edge of the adjustment ring protrudes from a lower end portion of the core in the +z direction,
first threads which form the screw portion is formed on an outer surface of the adjustment ring, and an engaging protruding portion is formed on an upper peripheral edge of the adjustment ring,
a side wall portion protruding in a circular cylindrical shape in the +z direction from an outer edge of the pedestal portion is formed on the base body, and second threads are formed on an inner wall of the side wall portion,
the first threads and the second threads threadedly engage with each other, and the engaging protruding portion of the adjustment ring is brought into contact with an upper end portion of the core, and
the core which is brought into contact with the engaging protruding portion is configured to be movable along the z axis due to the movement of the engaging protruding portion along the z axis caused by rotation of the adjustment ring,
the blood pump adjusting method comprising:
a blood pump preparation step of preparing the blood pump where at least a portion of the shaft on the +z direction side is exposed;
an adjustment jig mounting step having:
a step of holding the blood pump by a blood pump holder; and
a step of connecting a controller for controlling the blood pump to the blood pump; and
a runtime adjustment step having:
an F gauge contacting and pressing step of bringing a probe of a force gauge into contact with a center of rotation of the shaft from a +z direction side of the shaft and of pressing the probe;
a motor rotation step of rotating the motor of the blood pump at a predetermined condition;
a pressing force measurement step of measuring a pressing force by reading a value of the force gauge;
a first adjustment step of moving the core in the +z direction by rotating the adjustment ring in a first rotational direction in a case where it is determined that a measured pressing force is lower than a lower limit value of a predetermining control range; and
a second adjustment step of moving the core in a −z direction by rotating the adjustment ring in a second rotational direction opposite to the first rotational direction in a case where it is determined that the measured pressing force is higher than an upper limit value of the predetermining control range.

* * * * *